US007332176B1

(12) United States Patent
Valles et al.

(10) Patent No.: US 7,332,176 B1
(45) Date of Patent: Feb. 19, 2008

(54) SOLENOPSIS INVICTA VIRUSES

(75) Inventors: Steven M. Valles, Gainesville, FL (US);
Roberto M. Pereira, Gainesville, FL (US); Wayne B. Hunter, Port St. Lucie, FL (US); David H. Oi, Gainesville, FL (US); Charles A. Strong, Gainesville, FL (US); Phat M. Dang, Port St. Lucie, FL (US); David F. Williams, Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/239,183

(22) Filed: Sep. 29, 2005

(51) Int. Cl.
*A01N 63/00* (2006.01)
*A01N 25/00* (2006.01)
*A01N 25/08* (2006.01)
*C12N 7/02* (2006.01)
*C12N 15/01* (2006.01)

(52) U.S. Cl. .................... 424/405; 424/410; 424/93.6; 435/91.33; 435/239; 435/442

(58) Field of Classification Search .................... None
See application file for complete search history.

(56) References Cited

U.S. PATENT DOCUMENTS

| 4,925,663 | A  | 5/1990  | Stimac ................. 424/93   |
| 5,683,689 | A  | 11/1997 | Stimac ................. 424/93.5 |
| 6,254,864 | B1 | 7/2001  | Stimac ................. 424/93.5 |
| 6,369,078 | B1 | 4/2002  | Bowen et al. .......... 514/315   |
| 6,403,085 | B1 | 6/2002  | Stimac ................. 424/93.5 |
| 6,660,290 | B1 | 12/2003 | Stamets ................ 424/406  |

OTHER PUBLICATIONS

Williams et al., Biological Control od Imported Fire Ants, American Entomologist, 2003, vol. 49, No. 3, pp. 150-163.*
Avery et al., Virus-Like Particles in a Fire Ant, *Solenopsis* sp., (Hymenoptera:Formicidae) From Brazil, The Florida Entomologist, 1977, vol. 60, No. 1, pp. 17-20. See IDS p. 5.*
Valles et al., A picorna-like virus from the red imported fire ant, *Solenopsis invicta*: initital discovery, genme sequence, and characterization, Virology, Oct. 2004, vol. 328, No. 1, pp. 151-157. See IDS p. 6.*
Valles and Strong, *Solenopsis invicta* virus-1A (SINV-1A); Distinct species or genotype of SINV-1, Journal of Invertebrate Pathology, Mar. 2005, vol. 88, pp. 232-237. See IDS p. 6.*
Koonin, E.V., et al., Article, "Evolution and Taxonomy of Positive-Strand RNA Viruses: Implications of Comparative Analysis of Amino Acid Sequences", *Critical Reviews in Biochemistry and Molecular Biology*, vol. 28(5), pp. 375-430, 1993.
Koonin, E.V., et al., Article, "Diverse Groups of Plant RNA and DNA Viruses Share Related Movement Proteins that May Possess Chaperone-Like Activity", *J. General Virology*, vol. 72, pp. 2895-2903, 1991.

E.V. Koonin, Article, "The Phylogeny of RNA-Dependent RNA Polymerases of Positive-Strand RNA Viruses", *J. General Virology*, vol. 72, pp. 2197-2206, 1991.
"Virus Discovered in Fire Ants", Imported Fire Ant & Household Insects, USDA, ARS, CMAVE, http://cmave.usda.ufl.edu/ifahi/virus00.html, Nov. 11, 2004.
Excerpts from Steve Tvedten's Book "The Best Control (2nd Edition)", Alternative Controls of Fire Ants, http://www.thebestcontrol.com/fireants/ipm2.html, 3 pages.
Valles, S.M., et al., *GenBank*, Accession No. AY831776, "*Solenopsis invicata* virus-1A (SINV-1A): Distinct Species or Genotype of SINV-1?".
Valles, S.M., et al., *GenBank*, Accession No. AY634314, "A Picorna-Like Virus from the Red Imported Fire Ant, *Solenopsis invicta*: Initial Discovery, Genome Sequence, and Characterization".
Leat, N., et al., "Analysis of the Complete Genome Sequence of Black-Queen-Cell Virus, a Picorna-Like Virus of Honey Bees", *J. General Virology*, vol. 81, pp. 2111-2119, 2000.
Ghosh, R.C., et al., "The Nucleotide Sequence of Sacbrood Virus of the Honey Bee: an Insect Picorna-Like Virus", *J. Genral Virology*, vol. 80, pp. 1541-1549, 1999.
Ryan, M.D., et al., "Virus-Encoded Proteinases of the Picornavirus Super-Group", *J. General Virology*, vol. 78, pp. 699-723, 1997.
Krieger, M.J.B., et al., "Identification of a Major Gene Regulating Complex Social Behavior", *Science*, vol. 295, pp. 328-332, Jan. 11, 2002.
Sankar, S., et al., "Point Mutations Which Drastically Affect the Polymerization Activity of Encephalomyocarditis Virus RNA-Dependent RNA Polymerase Correspond to the Active Site of *Escherichia coli* DNA Polymerase I", *J. Biological Chemistry*, vol. 267(14), pp. 10168-10176, May 15, 1992.
Westra, D.F., et al., "Natural Infection with Herpes Simplex Virus Type 1 (HSV-1) Induces Humoral and T Cell Responses to the HSV-1 Glycoprotein H:L Complex", *J. General Virology*, vol. 81, pp. 2011-2015, 2000.
Govan, V.A., et al., "Analysis of the Complete Genome Sequence of Acute Bee Paralysis Virus Shows That it Belongs to the Novel Group of Insect-Infecting RNA Viruses", *Virology*, vol. 277, pp. 457-463, 2000.
Valles, S.M., et al., "Prevalence of *Thelohania solenopsae* (Microsporidia: Thelohaniidae) Infection in Monogyne and Polygyne Red Imported Fire Ants (Hymenoptera: Formicidae)", *Environmental Entomology*, vol. 33(2), pp. 340-345, Apr. 2004.
Pereira, R.M., et al., "Yellow-Head Disease Caused by a Newly Discovered *Mattesia* sp. In Populations of the Red Imported Fire Ant, *Solenopsis invicata*", *J. Invertebrate Pathology*, vol. 81, pp. 45-48, 2002.
R.M. Pereira, "Occurrence of *Myrmicinosporidium durum* in Red Imported Fire Ant, *Solenopsis invicata*, and Other New Host Ants in Eastern United States", *J. Invertebrate Pathology*, vol. 86, pp. 38-44, 2004.

(Continued)

*Primary Examiner*—Bruce R. Campell
*Assistant Examiner*—Sharon Hurt
(74) *Attorney, Agent, or Firm*—John D. Fado; Gail E. Poulos

(57) ABSTRACT

Unique *Solenopsis invicta* viruses (SINV) have been identified and their genome sequenced. Oligonucleotide primers have been developed using the isolated nucleic acid sequences of the SINV. The viruses are used as a biocontrol agent for control of fire ants.

6 Claims, 18 Drawing Sheets

OTHER PUBLICATIONS

Valles, S.M., et al., "Use of Ribosomal DNA Sequence Data to Characterize and Detect a Neogregarine Pathogen of *Solenopsis invicata* (Hymenoptera: Formicidae)", *J. Invertebrate Pathology*, vol. 84, pp. 114-118, 2003.

Alves, S.B., et al., "*Beauveria bassiana* Yeast Phase on Agar Medium and its Pathogenicity Against *Diatraea saccharalis* (Lepidoptera: Crambidae) and *Tetranychus urticae* (Acari: Tetranychidae)", *J. Invertebrate Pathology*, vol. 81, pp. 70-77, 2002.

Avery, S.W., et al., "Virus-Like Particles in a Fire Ant, *Solenopsis* Sp., (Hymenoptera: Formicidae) from Brazil", *The Florida Entomologist*, vol. 60(1), pp. 17-20, 1977.

Valles, S.M., et al., "A Picorna-Like Virus from the Red Imported Fire Ant, *Solenopsis invicta*: Initial Discovery, Genome Sequence, and Characterization", *Virology*, vol. 328, pp. 151-157, 2004.

Valles, S.M., et al., "*Solenopsis invicata* virus-1A (SINV-1A): Distinct Species or Genotype of SINV-1?", *J. Invertebrate Pathology*, vol. 88, pp. 232-237, 2005.

Excerpts from Steve Tvedten's Book "The Best Control (2nd Edition)", Alternative Controls of Fire Ants, http://www.thebestcontrol.com/fireants/ipm2.html, 3 pages, 2005.

Valles, S.M., et al., *GenBank*, Accession No. AY831776, "*Solenopsis invicata* virus-1A (SINV-1A): Distinct Species or Genotype of SINV-1?", 2005.

Valles, S.M., et al., *GenBank*, Accession No. AY634314, "A Picorna-Like Virus from the Red Imported Fire Ant, *Solenopsis invicta*: Initial Discovery, Genome Sequence, and Characterization", 2004.

\* cited by examiner

A. Helicase

```
              Hel A                           Hel B                           Hel C
SINV-1  23   PRTQPVVMLFCESGVGKSG-42-QNVIYDDDPG-27-HMABLEDKRKTKFTSKILLMTSN
ABPV    53   PRTQPVVMLFCGSGCRGKSG-42-QNIVCKDDFG-27-BGABLEDKRKYKFTSKVILMTSN
SBV     1369 VRYEPVVLCIPCPAGIVGKSE-38-QFVVYPDEG-26-HMABLEEKK.IDGNPLIVILLCN
BQCV    441  VRNPPTLIFLICGETGVGKST-49-QLVFYPDDEN-27-HMABIEEKANTVRQSKVILCSSN
CPMV    483  VRKAFPTIFFPQGKSIGKSL-35-QPFMDDFA-23-NHFGHEEKG.ICFSDSQFVFSTN
HAV     1219 TRCPFVCTFHGKRFGGKSSL-36-QLVCLIDDIG-22-NHASLEEKGR.BFSSPFIIATSN
```

B. Cysteine protease

```
                       *                                    *
SINV-1  663  .HFDAHILGC-34-GESKEA-83-APTINGDGGAPH.INEPSYLR.KTLGIHVA
ABPV    1166 MDAPGHLVGR-33-GPSKEA-83-MPTINCDCGAPI.VINETQVIR.KPAGIHVA
SBV     2132 ALIPRHYYRA-34-SESTDL-79-YS.QQGACGSLCFISR.SQRP..TVCMBFA
BQCV    904  AVAPGHTLRI-46-LDSRDL-85-KSTISQDGGAPI.PVTNSKIGPGK.IGHETT.
CPMV    982  FKACKHFFTH-29-IPDSEL-81-APTIPBDGSLVTAHIGGHHK..IVGVBV..
HAV     1558 LFYPSHAYLF-31-VGFQDV-79-GRGLPFCMGGAYSSNQSION.ATLGIHVA.
```

C. RNA-dependent RNA polymerase

```
                     I                              II                        III                         IV
SINV-1  1052 LKDERPFIEKV.DALKTRVFSNGEMDFNLAFRKVFLGFHMENARIIDNEVAIGHNVYSRDNT-15-GDFSNFDGSLNA
ABPV    1566 LKDERRFIEKV.DQLKF.RPIEKN.DQLKF.VSNGEMDFSIFFKVYLGFHNHENARIINYSTG.VIVSICHNVVSDDN-15-GBFSTFDGSLNV
SBV     2522 LKDERRFIEKVRKYGGTKVFCNNPPIDYIVSMRQYTMHFVAAPHBQKFKLMHRVGHNVSTGNT-15-IDMSNEGPGFWA
BQCV    1317 KCG.SPSGAPIVVINVIAIIS.H.KSRMESNGPIDYLVNSKMVFANPIVFLSELKNVDEHSVGSNVYSHDHD-15-GDFEGCFPASEQS
CPMV    1357 WCKSL.PSGPHYLAIIINSVFNLVM-24-TVAYGDPAVV-41-RLADVSYHKRNPFVIDSF.QRYIAFLSLDVVLEMP
HAV     1904 ECG.IPSGFPVTVLNSIFEIHI-26-LVTKGDDNLI-40-RLERCDFHRTFVQRSS..TIIWDAFPEDKASLWSQL

V                    VI                                 VII                                VIII
SINV-1  1184 THS.QPSGNPATTPLNCLINSIGL-36-LISYGDDNVI-41-TLEKVSFLKRCPIYMHER.NCYDAFLDINTILEMI
ABPV    1700 THS.QPSGNPATTPLNCFINSMGL-30-IVSKGDDNVI-41-TIEDVQTFKRERKFRIDSKR.KVMEEFLCMDTILEMP
SBV     2659 KCG.SPSGCAPIVVINVIAIIS.H.KSRMESNGPIDYLVNSKMVFANPIVFLSELKNVDEHSVGSNVYSHDHD-15-GBFSTFDGSLNV
BQCV    1453 WCKSL.PSGPHYLAIIINSVFNLVM-24-TVAYGDPAVV-41-RLADVSYHKRNPFVIDSF.QRYIAFLSLDVVLEMP
CPMV    1491 ECG.IPSGFPVTVLNSIFEIHI-26-LVTKGDDNLI-40-RLERCDFHRTFVQRSS..TIIWDAFPEDKASLWSQL
HAV     2035 CGS.MPSGSPCTALLNSILNNVNL-22-...CKGDDVLI-40-PVSELTPLKRSPNLVBDRIRPALSEKTIWSLIAW.
```

D. Capsid protein

```
SINV-1  704  QLFQVFRATICFKLSVKHFGPHLGRLEIFDPG-27-VKHTLDLTNDSEITIKVPFISDR
ABPV    533  NMFSMWRATMCYRIALVNKAPHIGRLGIPFCPG-28-VKMIPDLMNDTEITIKVPFVSNK
BQCV    425  SMFKVTGSLVYTTKFVKKDYHSGRVEISPDF-12-YRIHVDLREKSFSVVIPFISFV
```

```
   1 catcgagatc tattgctacc cttccaaatg catatgaagt tgttggctga cttggttaag
  61 atggttgata cctcaggcgc atttgggacc aaacctcgaa cccaaccagt tgtgatttgg
 121 ttgtttggtg aaagtggcgt aggtaagtca ggcatgtcct ggccgctagc cattgatctg
 181 aataatattt tcatgacaaa taaggaagat gcccggaact tctcgcgcaa catatatatg
 241 cgaaatgttg agcaggagtt ttgggacaat tatcaaggac aaaacgtagt tatatatgat
 301 gattttggac aacgcaaaga ttcccaagca aaacccaacg aagaattcat ggaattgatt
 361 cgtacagcta acatcgctcc atatccttta catatggcac atttagaaga taaacgaaag
 421 actaaattta catcaaaaat tctacttatg acatccaacg tttttgaaca gagtgtagat
 481 tctttaacct ttcctgatgc tttccgtagg cgcattgacc tgtgtggtcg cgtgtccaat
 541 aaaccacaat ttaccaaacc aggtttttca aaagcaactg gtcaaactgt taaagattg
 601 gacaaagata gggttagaaa agaattcaat caagttattt caacagacgt ttatttaata
 661 gatttaattg acgcagagac tggtgatgtc attgaagaag gattggatta tgcagaattc
 721 ctagaacgag caacacagaa aactaacgaa gcattcaatc aatccgtaga attaaatgaa
 781 ttttagaga attatgcaga atcccgatat cgactagcaa caatgcaggt aggcgatgaa
 841 tttcatgact gtaataattt attacttatt aagatagaaa actttgatga tttacctagc
 901 aatacgcttt tatttgattc acaaggaaat tccaaatcta aacgagaaat tgaggaaaat
 961 ttacagaatg catgggtggc aatgaagaa gacacttcga tgtggcacga ttcttattat
1021 aattttagag atgacatagt gtataaaaag tataaaagat cagtatcaga tagagagttt
1081 acactaatga aggcatatga gtatttaag aaacaatctt ctaaatttt gaacgataca
1141 ctaacgtata tcaaagaaca cccatttaaa gctgtagctg gagtaatgat agcagttttt
1201 accttgatga ccataggcaa ttttggtct tcttctggt cgaaaccaga gagagatagg
1261 acaacaaaga tgacgggtcg tcagcarggt aatattgttg aattgcccta cagaggkgaa
1321 gaagcgatag atttaagaca tcttgaggaa aaacaattaa tagaytattt gcaccatttt
1381 acatcttcag cgttrgcagg ctcaacatat gcgttcatat ttaaccaacc caatgctgtt
1441 gcctacggta tcttaacagg tgccgtagaa acggcgattg tttatatata cgacaaattt
1501 aggcaacatg gtaaaactgt gacgccagag gttgaagcag caacttcagg tgattgtatg
1561 acgaaagtga aacctcgcgt cattctggag gccacaacat ccggtgatgc acaaacgcag
1621 tatagatcta aaccaaaaat tgaagcattc acgtcggcgg atgtaataac cattactaaa
1681 cccaaagtga tggttgaggc agtgtcatct ggcgatagta taactcaaaa caaacctaaa
```

Fig. 10a

```
1741 gctaagattg aggcaatgac atctggtgac tcacatacca tggtgaaacc taaggctaaa
1801 atagaagcac aaacttcagg agataatatt acaatagtga gacctaaaat actaacagaa
1861 ggagatatta taccagcgaa tatgcaaatg tggaaggatc aagttgcaca aaatttaatt
1921 acccatcgta ttttcaacaa tttatataaa atttcggcta ataattgttc agttcccttg
1981 atgcatggtc ttatggttaa aggacgtatt atgcttattc cagcccacat tttaggatgt
2041 ggtataaaag cagatactga aattaccatg gagaatatgt ttaaagttaa atttacattc
2101 cctttcaaga gcgttaaagt aacccgcata actaatcgac atggagagtc aaaggaagct
2161 tgtttatttg ggcttccaaa tttggttcat acgcattgtg atattactaa acatttttca
2221 gattcagaag caatgtcatc ttattcacgt gcggaagtta acttacccttt attgcgatat
2281 tcccaacatt tagatagctt tatagtacac attctttcag ctaatgatgc atttgcaatt
2341 gaccatccca taattcttaa tgatgtagac ttgggcaaac atgttgtgag aagagcattg
2401 gaatatacag caccaacaac aaacggcgat tgtggcgcac cattaatcat caatgaaccc
2461 tctgtcttgc gaaagatagc aggaattcat gttgcaggtg acgcccatgg acgagcttat
2521 tcagaatcaa ttacacaagc tgatttaact cgagcttatc ctgaatttcc agcgcgaatg
2581 caaatttgtc tggactggga taataaaatg aagtttcacc caattgagat taagcaagaa
2641 tacaccaaag ctgactttcc atatgctcca ggagacatgt ttggtcccat aggtaagtgc
2701 ccccaccagt tatttgagcc cggtaaaaca gatattcgac ctagtgtaat ttatggtaag
2761 gtaaaacctc ctattacgaa acccgctatt ttacggcatt ccgaagttaa tatgaaattt
2821 aagaatttgc aaaaatgtgc ttcaaacgta ccgtacatta tgaagattg gcttgaggaa
2881 gcatatttag atgtaaagca attatggaat tctaaaagaa atgatgcgtt tcggcggatt
2941 ttaacagatg aagaagtaat taaggaaat gatatttcag aatatatttc tagtataaat
3001 cgacaatcat ccccaggtta cccatggatt ttagatcgta accaggctt tccaggtaag
3061 actcaatggt ttgggaacga tgaagattac aaaattgatc ctgacgtgat gcaaaaagta
3121 catgaaagaa ttgaaaacgc aaaacaagga atacggaccc caactttttg ggttgacacg
```

Fig. 10b

```
3181 ctcaaggatg agcgacgacc tattgagaaa gttgatgcac tcaaaacacg cgtcttttcg
3241 aacggaccca tggattttaa tttggctttc cgcaaatatt ttctaggatt tatagcgcat
3301 ttaatggaaa atcgaataga taatgaagta gcaataggca ccaacgtata tagtagagat
3361 tggacaaaac tggctaagaa attaaaacag aaaggtaaga acgtttttgc aggggatttt
3421 tcaaattttg atggatcctt aaatgccatg attatgtatt tgtttgcccg gatggcaaac
3481 gaattctatg atgatggtaa tgacctgatc cgttatgttt taattgagga gattttgaat
3541 tcagtacatc tttgtgaaca attcttctat atgatgaccc attcccaacc atctggcaat
3601 cctgcaacca ctcccttaaa ttgcttgatc aattcgatag gtttgcggtt gtgtttcctc
3661 cggtgttttg aagaacacaa ggccttcttt atggaactta tgaagaaatt tggctgtaaa
3721 acacggatgg agctattcag attgctagta tcactgatat cctatggaga tgataatgta
3781 atcaatattc accccctgat ttcccattta ttcaatatga atacaatcac aaaatacttt
3841 gcggaatttg gatttacata tacagatgaa acaaagcaag taggaaaagg agtgcctgat
3901 tataaaactc tggaagaagt ttcgtttctc aagagaggat ttatcttcaa tgaggagcga
3961 aattgttatg atgcgccctt ggacatcaat acaattctag atgattaa ttgggtccgg
4021 aaagatttgg atcaagtgga gagcactaag attaattgtg aaaatgcaat tatggaattg
4081 gctatgcatc cacggggctgt ttttgataag tggaccccac agatcgagaa agctttttat
4141 gacaaaactg gcgtggtctt gaaccacaat tcwtatgacg gctattggca tttacgaaat
4201 atggaatact ttttataaaa cgtttctctt ctggttacca gcaacatagg aaattgtcgt
4261 tgaactacat gttgtaaggc tttagagaaa taagggagtg tcctatttag gatgaggtgc
4321 tccggtggca gccccaccaa aacctctagc gactaggaac agctatatcg ggttgctata
4381 gcagtcagga tgtcattctg gcgttccgaa atacccaaac ctgctcaatc aaacaatgcg
4441 aatactttg agacgaaaac ggcaacaacc tctgcttccc acgcacaatc ggaacttagc
4501 gagacgaccc cagaaaattc ccttaccaga caagaactca cagttttcca tgatgttgaa
4561 caacctcgcg tcgctcttcc aattgctccg caaacgacta gctctcttgc taagcttgat
4621 tctacagcga caattgtgga ttttctttct agaactgttg tcctcgatca attcgagctt
```

Fig. 10c

```
4681 gttcaaggtg aatcaaacga taaccacaaa cccettaacg cagcaactt  taaagacccc
4741 caaccagcca tcagacagta ttccttgcca ggagacattc ttaagctggg tggcaagtta
4801 gataaggcaa ataaccatca atactttaag gcagattgtc acataaaatt agttttaaat
4861 acaaatccca tggtggccgg aagattttgg ctaacatatt ccccatatga acataaagta
4921 gataaggcaa gacgccagca atataatagt agagctggag tgacagcata tcctggaata
4981 gaaatggatg ttcaaatcaa tgattcagca gaaatggtta tcccatttgc ttcctacaaa
5041 gaagcttatg atttaaatac tcccacccct gaagattttg ttacattatc tttattcggt
5101 ataacagatt tactagctaa aaatggtaat aattacgcag taggaattac catcttagcc
5161 tggtttgaaa acataacaat taatctacct acaataaaga atatcccata caggcaatta
5221 ccccacacca atactaatac taagaaaatt gaaatagatc gcaaattagc taaattagaa
5281 aagaagaatc cttcggccta taaatatata actaatattt tagatatacg accagccacc
5341 atgcaaaccg catggggtgc cccatcacag ttgctaatta aagatattct agatctagca
5401 ccagtgctta atgaacttca agcagtattg tctgatgtgt gtggatcaat taggaaccga
5461 gactttcgt  tgaggccctt gtataaagta cgcatacatg caatgcaaga cttaatcaat
5521 gattccctaa agaggatgtt tgatacatat gaggccctgg acgagacgga tcttatgagt
5581 gaagacacac cagataatgc ttttccaact atggttttat acttagattc ccttaagaaa
5641 attaacaagt caaaatcaga gtatgttgag atgcagttgg atgcctatga tgcacgggat
5701 attgatggta tgctgaatgc gtacgatcaa ttgaaagagt ttaaccatca tacagcaaga 5761 aaggaaatgg tgtcaatgat gcatctgggc taccaatatt ctcaacgacg acaccgacgt
5821 gatgtgacag cagcgagagc catagcggat atgatacttg tcgacgagcg tgatgcgacg
5881 atgcaagtgc aagcagaagt aggaggacag ggtttgatca ctgacatagc ttccaccgtt
5941 tcggcggtgg caggtgcggt cagtggtatc cctgtcatac gtgaaatagc atctaccgtt
6001 ggttgggttt ctgacatagt tggaggaatt tcctctatct ttggatggtc tcgaccaaat
6061 gatatggaga aagtgacatc tttggctaac gtccccggca agtattattc ccatgtaaaa
6121 gcgatagata atagtgtagc tttagctttg agtaatgaga acgagcttct cccacttagc
```

Fig. 10d

```
6181 gacatctttc cctcagcggt agatgagatg gacttggcat atgtgtgtgc taatcctgga
6241 gtgaaggaag tcattacgcg gtcgaaaacg gacccyatga atagaacttt agctttaatg
6301 gaagtgggat tacctagttt taatagatac caagataagg caatagattg tgatagtgaa
6361 cctaccccat ataatatctg taacaaagrt ttgatcaaac caaatgggaa catcattttg
6421 agccctggag atctggtgca gatgaagggc agcttggctg cgacaatttt ggatactgtt
6481 ccttgtgaat atgtgtccca attgtttcag tattggcgtg ctaccatttg ctttaagatt
6541 tctgtggtaa agaccggttt tcatacagga cgtttagaaa ttttctttga cccgggtgag
6601 tatctaacga atcctaaggc ggattggcat aattatgttg atctttccgc ttacgataaa
6661 gtggataccg caaattctta caaatatatt ttagatttaa caaatgattc agaaattact
6721 attagagtgc catttattag cgataggtta gctttaagta caattggtgc taatagttat
6781 ggtgaggacg gtgtaatggg accccaaat ttgaatgata ttttcgattc aatgattggg
6841 tctctaatca tcagaccgct tacaaaactt atggcgccag atacagtttc agatcaagtt
6901 aaaatagtaa tttggaaatg ggcagaggat gtacagctcc ttgttcccaa agaatcgaac
6961 cagctcgaaa tagttccata cgagttcgag cgaacaccag gtttgacctg caagaaacag
7021 aaaatatcag atgaagatat gaaggtgttt attgcacatt gggaaaaaga tggcaaatgg
7081 atttgtactt cagacccaac tacaagcatg gttttctcat ggggacaata tcccttatgt
7141 gagactagaa atgccacaat gcagatcaac atttccaatg aagcatcagg aaacagtatc
7201 gatattttcc aggataataa tgcaggtgtg agtccaaatg cagtaatggg taaaattgcg
7261 ggtgaacgtc tagttaactt gcgaccacta ctgcgctgct tccgatcttt ggtggcata
7321 acgcttgatc gggcaggaca aattctgtct gaaagagtgt attggaacca caaagattat
7381 gttagcatac tctcatatct gtatcgtttt ccagagggg gatatcgtta caaattcttt
7441 gcagacgata acgaacaggg acaagtcatg tcaacgcttg tcaaaaatta ctacaaggac
7501 catgcaacaa gtactggtcc atcccatatg acttacaata atattaatcc cgtacatgaa
7561 attatgatcc catattattc tcaatatagg aaaatcccaa tttcaggcga agtagaatta
7621 attaaaggta agattcaaac tcccgtagaa aagggcatta aggtgagct ttatcgctca
7681 ggaaatgatg acctaaccta tgggtggatc gttggatcgc cccagcttta tgttggagcg
7741 gctcaacgat ggagttgttg gacagtaaca aagccaacac aactagtcac taaggaaact
7801 taatggatag taaattttgc tcttcaaaga cagtcaaatc tttggagttc ggttttattc
7861 ttcaaaattc ttttaaaaca gaggatgcat agttaatggc gagcactatc gtccggaatg
7921 acaccgttga gaaaactcac tagatggagg ctcattggtt atcagcgttc tgggataatc
7981 taacgattag ttatgcaaac gcatattcaa gtaaattaca attaag
```

Fig. 10e

```
   1 taatctacct acaataaaga atatcccata tagacaatta ccccaaacta ataccaatgc
  61 aaagaagatt gaaatagatc gaaaattggc taaattagaa aagaagaacc cttccgctta
 121 taaatatata actaatattt tagatatacg gccggccacc atgcagaccg catggggcac
 181 tccatcacaa ttattaatta aggatgtttt agatttagca ccggtattta acgaacttca
 241 agcagtatta tctgaagtgt gtggatcaat taggaaccga gacttttcgt tgaggccttt
 301 atataaagta cgcatacatg ctatgcaaga cttaatcaat gattccttaa agaggatgtt
 361 tgatagatat gaggccctgg acgagacgga tcttatgagt gaagacacac cagataatgc
 421 tttcccaact atggttttat atttggattc ccttaagaaa attaataagt caaaatcaga
 481 gtatgtggag atgcaattgg atgcctatga tgcacgagat attgatggta tgttaaatgc
 541 atataatcaa ttgaaagagt ttaatcacca tacagcaaga aaggagatgg tgtcaatgat
 601 gcatctgggt tatcaatatt cccaacggcg gcaccgacga gatgtaacag cagcaagagc
 661 catagcagat acaatacttg tagatgaacg cgatgcaaca atgcaagtcc aagcagaagt
 721 aggaggacag ggtcttatta ctgacatagc ctctaccgtt tcggcggtgg cgggtgcagt
 781 cagtggtatc ccggttatag gagaaattgc atctacagtt ggttgggttt ctgatatagt
 841 tggaggaatt tcctccatct ttggatggtc tcgaccaaat gacatggaaa aagtaacatc
 901 tttggcaaac gttcctggca agtattattc tcacgtaaaa gcagtagata atagtgtagc
 961 tttagctttg agtaatgaga acgaacttct cccgcttagt gacatctttc cctcagcagt
1021 agatgagatg gatttggcat acgtgtgtgc caacccccgga gtgaaggagg tcattacatg
1081 gtcgaagaca gatcccatga ataagacttt agcattaatg gaagtaggat tacctagttt
1141 taatagatat caggataagg caatagattg tgatagtgaa cccactccat acaacatttg
1201 taataaagat ttaattaaac caaatgggaa tattattttg agccctgggg atctggtgca
1261 gatgaaaggt agcctggctg cgacaatctt ggacactgtt ccatgcgaat acgtgtctca
1321 gttgtttcag tattggcgtg ctacaatttg ctttaagatt tccgtggtga aaactggttt
1381 ccatacagga cgtttggaga ttttcttttga ccctggtgag tatcttacta atcctaaggc
1441 ggattggcat aattatgttg atctttcggc ttatgataag gtggatactg caaattctta
1501 caaatatatt ttagatttaa cgaatgattc agaaattacc attagagtac catttattag
1561 tgataggtta gctttaagca aatcggtgc caatagttat ggtgaggatg gtgtgatggg
1621 accccaaat ttgaacgata ttttcgattc aatgattggg tctctgatca tcaggccgct
1681 cacgaggctt atggcgccag atacagtttc agatcaggtt aaaatagtaa tttggaaatg
1741 ggctgaagat gtgcagctcc ttgttcctaa agaatcaaat caactcgaaa tcgttccata
1801 cgagtttgag cgaacaccag gtttgacatg caagaaacaa aagatttctg atcaagatat
1861 gaaggtgttt attgcgcatt gggaaaaaga tggtcaatgg gtttgtactt cagacccaac
1921 cacaagcatg gtcttttcat ggggacaata tcccttatgt gagaccagaa atgctacgat
1981 gcagataaac atttctaatg aagcttcagg aaatagtatt gatattttcc aggataataa
2041 tgcaggtgta agtccaaacg cagttatggg gaaaattgca ggtgaacgtt tagttaacct
2101 acgaccatta ttgcgatgct ttcgttcctt gggtggcata acgctggatc gggcaggtca
2161 aatcctgtct gagagagtgt attggcatta taaggattac gttagcatac tttcatacct
2221 gtatcgattt tctagaggag gatatcgcta caagtttttt gcagatgaca acgaacaagg
2281 acaagtcatg tcaacgcttg ttaaaaatta ccacaaggac catgctacaa gcactggtcc
2341 ttcccatatg acttacaata atctcaaccc cgtacacgaa attatgatcc catattattc
2401 tcaatatagg aaaattccaa tttcaggcga agtagaatta attaaaggta agattcagac
2461 acctgtagaa aagggcatta aggtgagct ttatcgctca ggaaatgatg acctgacata
2521 cgggtggatc gttggatcgc cccaacttta tgttggagca gctcaacggt ggagttgttg
2581 gacagtaaca aagccaacac aactaggcac taaggaaact taatggatag taaattttgc
2641 tcttcaggga cagtcaaatc tctggagttc ggttttattc ttcaaaattc ttttaaaaca
2701 gaggacgtat gtggaatggc gagcactatt gttcggattg acgatttga gaaaactcac
2761 tagatggagg ctcttgatct attagcagtc tgagataatc taacgatttc acatgcgaac
2821 gcatattcaa gtaaattaaa ttaagaaaaa aaaaaaaaa aaaa
```

Fig. 11 tgtctgaaag agtgtattgg aaccacaaag attatgttag catactctca tatctgtatc
gtttttccag aggggatat cgttacaaat tcttcgcaga cgataacgga cagggacaag
tcatgtcaac gcttgtcaaa aattactaca aggaccatgc aacaagtact ggtccatccc
atatgactta caataatatt aatcccgtac atgaaattat gatcccatat tactctcaat
ataggaaaat cccaatttca ggcgaagtag aattgattaa aggtaagatt caaactcccg
tagaaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattctttta aaacagagga
tgcatagtta atggcgagca ctatcgtccg gaatgacacc tttgagaaaa ctcactagat
gga

Fig. 12 tgtctgaaag agtgtattgg aaccacaaag attatgttag catactctca tatctgtatc
gtttttccag aggggatat cgttacaaat tcttcgcaga tgataacgaa cagggacaag
tcatgtcaac gcttgtcaaa aattactaca aggaccatgc aacaagtact ggtccatccc
atatgactta caataatatt aatcccgtac atgaaattat gatcccatat tattctcaat
ataggaaaat cccaatttca ggcgaagtag aattaattaa aggtaagatt caaactcccg
tagaaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattctttta aaacagagga
tgcatagtta atggcgagca ctatcgtccg gaatgacacc tttgagaaaa ctcactagac
gga

Fig. 13 tgtctgaaag agtgtattgg aatcacaaag attatgttag catactctca tatctgtatc
gtttttccag aggggatat cgttacaaat tcttcgcaga cgataacgaa cagggacaag
tcatgtcaac gcttgtcaaa aattactaca aggaccatgc aacaagtact ggtccatccc
atatgactta caataatatt aatcccgtac atgagattat gatcccatat tattctcaat
ataggaaaat cccaatttca ggcgaagtag aattaattaa aggtaagatt caaactcccg
tagaaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
gaagacagtc aaatctttgg agttcggttt tattcttcaa aattctttta aaacagagga
tgcatagtta atggcgagca ctatcgtccg gaatgacacc tttgagaaaa ctcactagat
gga

Fig. 14 tgtctgaaag agtgtattgg aaccacaaag attatgttag catactctca tatctgtatc
gtttttccag aggggatat cgttacaaat tcttcgcaga cgataacgaa cagggacaag
tcatgtcaac gcttgtcaaa aattactaca aggaccatgc aacaagtact ggtccatccc
atatgactta caataatatt aatcccgtac atgaaattat gatcccatat tattctcaat
ataggaaaat cccaatttca ggcgaagtag aattaattaa aggtaagatt caaactcccg
tagaaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattctttta aaacagagga
tgcatagtta atggcgagca ctatcgtctg gaatgacacc attgagaaaa ctcactagat
gga

Fig. 15 tgtctgaaag agtgtattgg aatcacaaag attatgttag catactctca tatctgtatc
gtttttccag aggggggatat cgttacaaat tcttcgcaga cgataacgaa cagggacaag
tcatgtcaac gcttgtcaaa aattactaca aggaccatgc aacaagtact ggtccatccc
atatgactta caataatatt aatcccgtac atgagattat gatcccatat tattcccaat
ataggaaaat cccaatttca ggcgaagtag aattaattaa aggtaagatt caaactcccg
tagaaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattctttta aaacagagga
tgcatagtta atggcgagca ctatcgtccg gaatgacacc tttgagaaaa ctcactagat
gga

Fig. 16 cactccatac aacatttgta ataaagattt aattaaacca aatgggaata ttgttttgag
ccctggggat ctggtgcaga tgaaaggtag cctggctgcg acaattttag acactgttcc
atgtgaatac gtgtctcagt tgtttcagta ttgg

Fig. 17 cactccatac aacatttgta ataaagattt aattaaacca aatgggaata tcattttgag
ccctggggat ctggtgcaga tgaagggtag cctggctgcg acaattttgg acactgttcc
atgtgaatac gtgtctcagt tgtttcagta aagg

Fig. 18

SEQUENCE LISTING

```
<160> NUMBER OF SEQ ID NOS: 46

<210> SEQ ID NO 1
<211> LENGTH: 8026
<212> TYPE: DNA
<213> ORGANISM: Solenopsis Invicta Virus
<300> PUBLICATION INFORMATION:
<301> AUTHORS: Steven M. Valles et al.
<302> TITLE: A picorna-like virus from the red imported fire ant,
      Solenopsis invicta: initial discovery, genome sequence, and
      characterization
<303> JOURNAL: Virology
<304> VOLUME: 328
<306> PAGES: 151-157
<307> DATE: 2004-08-21
<300> PUBLICATION INFORMATION:
<308> DATABASE ACCESSION NUMBER: GenBank/AY634314
<309> DATABASE ENTRY DATE: 2004-09-29
<313> RELEVANT RESIDUES: (28)..(4218)
<300> PUBLICATION INFORMATION:
<308> DATABASE ACCESSION NUMBER: GenBank/AY634314
<309> DATABASE ENTRY DATE: 2004-09-29
<313> RELEVANT RESIDUES: (4390)..(7803)

<400> SEQUENCE: 1
catcgagatc tattgctacc cttccaaatg catatgaagt tgttggctga cttggttaag      60
atggttgata cctcaggcgc atttgggacc aaacctcgaa cccaaccagt tgtgatttgg     120
ttgtttggtg aaagtggcgt aggtaagtca ggcatgtcct ggcccctagc cattgatctg     180
aataatattt tcatgacaaa taaggaagat gcccggaact tctcgcgcaa catatatatg     240
cgaaatgttg agcaggagtt ttgggacaat tatcaaggac aaaacgtagt tatatatgat     300
gattttggac aacgcaaaga ttcccaagca aaacccaacg aagaattcat ggaattgatt     360
cgtacagcta acatcgctcc atatccttta catatggcac atttagaaga taaacgaaag     420
actaaattta catcaaaaat tctacttatg acatccaacg tttttgaaca gagtgtagat     480
tctttaacct ttcctgatgc tttccgtagg cgcattgacc tgtgtggtcg cgtgtccaat     540
aaaccacaat ttaccaaacc aggtttttca aaagcaactg gtcaaactgt taaaagattg     600
gacaaagata gggttagaaa agaattcaat caagttattt caacagacgt ttatttaata     660
gatttaattg acgcagagac tggtgatgtc attgaagaag gattggatta tgcagaattc     720
ctagaacgag caacacagaa aactaacgaa gcattcaatc aatccgtaga attaaatgaa     780
tttttagaga attatgcaga atcccgatat cgactagcaa caatgcaggt aggcgatgaa     840
tttcatgact gtaataattt attacttatt aagatagaaa actttgatga tttacctagc     900
```

```
aatacgcttt tatttgattc acaaggaaat tccaaatcta aacgagaaat tgaggaaaat    960
ttacagaatg catgggtggc aatggaagaa gacacttcga tgtggcacga ttcttattat   1020
aattttagag atgacatagt gtataaaaag tataaaagat cagtatcaga tagagagttt   1080
acactaatga aggcatatga gtattttaag aaacaatctt ctaaattttt gaacgataca   1140
ctaacgtata tcaaagaaca cccatttaaa gctgtagctg gagtaatgat agcagttttt   1200
accttgatga ccataggcaa tttttggtct tctttctggt cgaaaccaga gagagatagg   1260
acaacaaaga tgacgggtcg tcagcarggt aatattgttg aattgcccta cagaggkgaa   1320
gaagcgatag atttaagaca tcttgaggaa aaacaattaa tagaytattt gcaccatttt   1380
acatcttcag cgttrgcagg ctcaacatat gcgttcatat ttaaccaacc caatgctgtt   1440
gcctacggta tcttaacagg tgccgtagaa acggcgattt tttatatata cgacaaattt   1500
aggcaacatg gtaaaactgt gacgccagag gttgaagcag caacttcagg tgattgtatg   1560
acgaaagtga aacctcgcgt cattctggag gccacaacat ccggtgatgc acaaacgcag   1620
tatagatcta aaccaaaaat tgaagcattc acgtcggcgg atgtaataac cattactaaa   1680
cccaaagtga tggttgaggc agtgtcatct ggcgatagta taactcaaaa caaacctaaa   1740
gctaagattg aggcaatgac atctggtgac tcacatacca tggtgaaacc taaggctaaa   1800
atagaagcac aaacttcagg agataatatt acaatagtga gacctaaaat actaacagaa   1860
ggagatatta taccagcgaa tatgcaaatg tggaaggatc aagttgcaca aaatttaatt   1920
acccatcgta ttttcaacaa tttatataaa atttcggcta ataattgttc agttcccttg   1980
atgcatggtc ttatggttaa aggacgtatt atgcttattc cagcccacat tttaggatgt   2040
ggtataaaag cagatactga aattaccatg gagaatatgt ttaaagttaa atttacattc   2100
cctttcaaga gcgttaaagt aacccgcata actaatcgac atggagagtc aaaggaagct   2160
tgtttatttg ggcttccaaa tttggttcat acgcattgtg atattactaa acattttttca  2220
gattcagaag caatgtcatc ttattcacgt gcggaagtta acttacctttt attgcgatat  2280
tcccaacatt tagatagctt tatagtacac attcttcag ctaatgatgc atttgcaatt   2340
gaccatccca taattcttaa tgatgtagac ttgggcaaac atgttgtgag aagagcattg   2400
gaatatacag caccaacaac aaacggcgat tgtggcgcac cattaatcat caatgaaccc   2460
tctgtcttgc gaaagatagc aggaattcat gttgcaggtg acgcccatgg acgagcttat   2520
tcagaatcaa ttcacaagc tgatttaact cgagcttatc ctgaatttcc agcgcgaatg   2580
caaatttgtc tggactggga taataaaatg aagtttcacc caattgagat taagcaagaa   2640
tacaccaaag ctgactttcc atatgctcca ggagacatgt ttggtcccat aggtaagtgc   2700
ccccaccagt tatttgagcc cggtaaaaca gatattcgac ctagtgtaat ttatggtaag   2760
gtaaaacctc ctattacgaa acccgctatt ttacggcatt ccgaagttaa tatgaaattt   2820
aagaatttgc aaaaatgtgc ttcaaacgta ccgtacatta tgaagattg gcttgaggaa   2880
gcatatttag atgtaaagca attatggaat tctaaaagaa atgatgcgtt tcggcggatt   2940
ttaacagatg aagaagtaat taaggaaat gatatttcag aatatatttc tagtataaat   3000
cgacaatcat ccccaggtta cccatggatt ttagatcgta accaggctt tccaggtaag   3060
actcaatggt ttgggaacga tgaagattac aaaattgatc ctgacgtgat gcaaaaagta   3120
catgaaagaa ttgaaaacgc aaaacaagga atacggaccc caacttttttg ggttgacacg  3180
ctcaaggatg agcgacgacc tattgagaaa gttgatgcac tcaaaacacg cgtcttttcg   3240
aacggaccca tggattttaa tttggctttc cgcaaatatt ttctaggatt tatagcgcat   3300
```

```
ttaatggaaa atcgaataga taatgaagta gcaataggca ccaacgtata tagtagagat    3360
tggacaaaac tggctaagaa attaaaacag aaaggtaaga acgttttgc aggggatttt     3420
tcaaattttg atggatcctt aaatgccatg attatgtatt tgtttgcccg gatggcaaac    3480
gaattctatg atgatggtaa tgacctgatc cgttatgttt taattgagga gattttgaat    3540
tcagtacatc tttgtgaaca attcttctat atgatgaccc attcccaacc atctggcaat    3600
cctgcaacca ctcccttaaa ttgcttgatc aattcgatag gtttgcggtt gtgtttcctc    3660
cggtgttttt aagaacacaa ggccttcttt atggaactta tgaagaaatt tggctgtaaa    3720
acacggatgg agctattcag attgctagta tcactgatat cctatggaga tgataatgta    3780
atcaatattc accccctgat ttcccattta ttcaatatga atacaatcac aaaatacttt    3840
gcggaatttg gatttacata tacagatgaa acaaagcaag taggaaaagg agtgcctgat    3900
tataaaactc tggaagaagt ttcgtttctc aagagaggat ttatcttcaa tgaggagcga    3960
aattgttatg atgcgccctt ggacatcaat acaattctag atgattaa ttgggtccgg      4020
aaagatttgg atcaagtgga gagcactaag attaattgtg aaaatgcaat tatgaaattg    4080
gctatgcatc cacgggctgt ttttgataag tggaccccac agatcgagaa agctttttat    4140
gacaaaactg gcgtggtctt gaaccacaat tcwtatgacg gctattggca tttacgaaat    4200
atggaatact ttttataaaa cgtttctctt ctggttacca gcaacatagg aaattgtcgt    4260
tgaactacat gttgtaaggc tttagagaaa taagggagtg tcctatttag gatgaggtgc    4320
tccggtggca gccccaccaa aacctctagc gactaggaac agctatatcg ggttgctata    4380
gcagtcagga tgtcattctg gcgttccgaa atacccaaac ctgctcaatc aaacaatgcg    4440
aatactttg agacgaaaac ggcaacaacc tctgcttccc acgcacaatc ggaacttagc     4500
gagacgaccc cagaaaattc ccttaccaga caagaactca cagttttcca tgatgttgaa    4560
caacctcgcg tcgctcttcc aattgctccg caaacgacta gctctcttgc taagcttgat    4620
tctacagcga caattgtgga ttttctttct agaactgttg tcctcgatca attcgagctt    4680
gttcaaggtg aatcaaacga taaccacaaa ccccttaacg cagcaacttt taaagacccc    4740
caaccagcca tcagacagta ttccttgcca ggagacattc ttaagctggg tggcaagtta    4800
gataaggcaa ataaccatca atactttaag gcagattgtc acataaaatt agttttaaat    4860
acaaatccca tggtggccgg aagatttttgg ctaacatatt ccccatatga acataaagta   4920
gataaggcaa gacgccagca atataatagt agagctggag tgacagcata tcctggaata    4980
gaaatggatg ttcaaatcaa tgattcagca gaaatggtta tcccatttgc ttcctacaaa    5040
gaagcttatg atttaaatac tcccacccct gaagattttg ttacattatc tttattcggt    5100
ataacagatt tactagctaa aaatggtaat aattacgcag taggaattac catcttagcc    5160
tggtttgaaa acataacaat taatctacct acaataaaga atatcccata caggcaatta    5220
ccccacacca atactaatac taagaaaaatt gaaatagatc gcaaattagc taaattagaa    5280
aagaagaatc cttcggccta taaatatata actaatattt tagatatacg accagccacc    5340
atgcaaaccg catggggtgc cccatcacag ttgctaatta aagatattct agatctagca    5400
ccagtgctta tgaacttca agcagtattg tctgatgtgt gtggatcaat taggaaccga    5460
gacttttcgt tgaggcccctt gtataaagta cgcatacatg caatgcaaga cttaatcaat    5520
gattccctaa agaggatgtt tgatacatat gaggccctgg acgagacgga tcttatgagt    5580
gaagacacac cagataatgc ttttccaact atggttttat acttagattc ccttaagaaa    5640
```

```
attaacaagt caaaatcaga gtatgttgag atgcagttgg atgcctatga tgcacgggat    5700
attgatggta tgctgaatgc gtacgatcaa ttgaaagagt ttaaccatca tacagcaaga    5760
aaggaaatgg tgtcaatgat gcatctgggc taccaatatt ctcaacgacg acaccgacgt    5820
gatgtgacag cagcgagagc catagcggat atgatacttg tcgacgagcg tgatgcgacg    5880
atgcaagtgc aagcagaagt aggaggacag ggtttgatca ctgacatagc ttccaccgtt    5940
tcggcggtgg caggtgcggt cagtggtatc cctgtcatac gtgaaatagc atctaccgtt    6000
ggttgggttt ctgacatagt tggaggaatt cctctatct ttggatggtc tcgaccaaat    6060
gatatggaga aagtgcacatc tttggctaac gtccccggca agtattattc ccatgtaaaa    6120
gcgatagata atagtgtagc tttagctttg agtaatgaga cgagcttct cccacttagc    6180 gacatctttc cctcagcggt agatgagatg gacttggcat atgtgtgtgc taatcctgga    6240
gtgaaggaag tcattacgcg gtcgaaaacg gacccyatga atagaacttt agctttaatg    6300
gaagtgggat tacctagttt taatagatac caagataagg caatagattg tgatagtgaa    6360
cctaccccat ataatatctg taacaaagrt ttgatcaaac caaatgggaa catcattttg    6420
agccctggag atctggtgca gatgaagggc agcttggctg cgacaatttt ggatactgtt    6480
ccttgtgaat atgtgtccca attgtttcag tattggcgtg ctaccatttg ctttaagatt    6540
tctgtggtaa agaccggttt tcatacagga cgtttagaaa ttttctttga cccgggtgag    6600
tatctaacga atcctaaggc ggattggcat aattatgttg atctttccgc ttacgataaa    6660
gtggataccg caaattctta caaatatatt ttagatttaa caaatgattc agaaaattact    6720 attagagtgc catttattag cgataggtta gctttaagta caattggtgc taatagttat    6780
ggtgaggacg gtgtaatggg accccccaaat ttgaatgata ttttcgattc aatgattggg    6840
tctctaatca tcagaccgct tacaaaactt atggcgccag atacagtttc agatcaagtt    6900
aaaatagtaa tttggaaatg ggcagaggat gtacagctcc ttgttcccaa agaatcgaac    6960
cagctcgaaa tagttccata cgagttcgag cgaacaccag gtttgacctg caagaaacag    7020
aaaatatcag atgaagatat gaaggtgttt attgcacatt gggaaaaaga tgcaaaatgg    7080
atttgtactt cagacccaac tacaagcatg gtttttctcat ggggacaata tcccttatgt    7140
gagactagaa atgccacaat gcagatcaac atttccaatg aagcatcagg aaacagtatc    7200 gatatttcc aggataataa tgcaggtgtg agtccaaatg cagtaatggg taaaattgcg    7260
ggtgaacgtc tagttaactt gcgaccacta ctgcgctgct tccgatcttt gggtggcata    7320
acgcttgatc gggcaggaca aattctgtct gaaagagtgt attggaacca caaagattat    7380
gttagcatac tctcatatct gtatcgtttt tccagagggg gatatcgtta caaattcttt    7440
gcagacgata acgaacaggg acaagtcatg tcaacgcttg tcaaaaatta ctacaaggac    7500
catgcaacaa gtactggtcc atcccatatg acttacaata atattaatcc cgtacatgaa    7560
attatgatcc catattattc tcaatatagg aaaatcccaa tttcaggcga agtagaatta    7620
attaaaggta agattcaaac tcccgtagaa aagggcatta aggtgagct ttatcgctca    7680 ggaaatgatg acctaaccta tgggtggatc gttggatcgc cccagctta tgttggagcg    7740 gctcaacgat ggagttgttg gacagtaaca aagccaacac aactagtcac taaggaaact    7800
taatggatag taaattttgc tcttcaaaga cagtcaaatc tttggagttc ggttttattc    7860
ttcaaaattc tttaaaaaca gaggatgcat agttaatggc gagcactatc gtccggaatg    7920
acaccgttga gaaaactcac tagatggagg ctcattggtt atcagcgttc tgggataatc    7980
taacgattag ttatgcaaac gcatattcaa gtaaattaca attaag               8026
```

```
<210> SEQ ID NO 2
<211> LENGTH: 25
<212> TYPE: DNA
<213> ORGANISM: Solenopsis Invicta Virus

<400> SEQUENCE: 2
ggaagtcatt acgtggtcga aaacg                                           25

<210> SEQ ID NO 3
<211> LENGTH: 39
<212> TYPE: DNA
<213> ORGANISM: Solenopsis Invicta Virus

<400> SEQUENCE: 3
cgtcctgtat gaaaaccggt ctttaccaca gaaatctta                            39

<210> SEQ ID NO 4
<211> LENGTH: 24
<212> TYPE: DNA
<213> ORGANISM: Solenopsis Invicta Virus

<400> SEQUENCE: 4
ggaagtcatt acgtggtcga aaac                                            24

<210> SEQ ID NO 5
<211> LENGTH: 28
<212> TYPE: DNA
<213> ORGANISM: Solenopsis Invicta Virus

<400> SEQUENCE: 5
ccaagctgcc cttcatctgc accagatc                                        28

<210> SEQ ID NO 6
<211> LENGTH: 27
<212> TYPE: DNA
<213> ORGANISM: Solenopsis Invicta Virus

<400> SEQUENCE: 6
ttcatctgca ccagatctcc agggctc                                         27

<210> SEQ ID NO 7
<211> LENGTH: 26
<212> TYPE: DNA
<213> ORGANISM: Solenopsis Invicta Virus

<400> SEQUENCE: 7
caatgattca gcagaaatgg ttatcc                                          26

<210> SEQ ID NO 8
<211> LENGTH: 21
<212> TYPE: DNA
<213> ORGANISM: Solenopsis Invicta Virus

<400> SEQUENCE: 8
gtcacatcac gtcggtgtcg t                                               21

<210> SEQ ID NO 9
<211> LENGTH: 20
<212> TYPE: DNA
<213> ORGANISM: Solenopsis Invicta Virus

<400> SEQUENCE: 9
```

-continued tctgccttaa agtattgatg  20

<210> SEQ ID NO 10
<211> LENGTH: 33
<212> TYPE: DNA
<213> ORGANISM: Solenopsis Invicta Virus

<400> SEQUENCE: 10
gtctcctggc aaggaatact gtctgatggc tgg  33

<210> SEQ ID NO 11
<211> LENGTH: 29
<212> TYPE: DNA
<213> ORGANISM: Solenopsis Invicta Virus

<400> SEQUENCE: 11
ggaagagcga cgcgaggttg ttcaacatc  29

<210> SEQ ID NO 12
<211> LENGTH: 31
<212> TYPE: DNA
<213> ORGANISM: Solenopsis Invicta Virus

<400> SEQUENCE: 12
cgcatcaact ttctcaatgg gtcgtcgctc a  31

<210> SEQ ID NO 13
<211> LENGTH: 23
<212> TYPE: DNA
<213> ORGANISM: Solenopsis Invicta Virus

<400> SEQUENCE: 13
cagtgatact agcaatctga ata  23

<210> SEQ ID NO 14
<211> LENGTH: 22
<212> TYPE: DNA
<213> ORGANISM: Solenopsis Invicta Virus

<400> SEQUENCE: 14
ctatctaaat gttgggaata tc  22

<210> SEQ ID NO 15
<211> LENGTH: 28
<212> TYPE: DNA
<213> ORGANISM: Solenopsis Invicta Virus

<400> SEQUENCE: 15
caccggatgt tgtggcctcc agaatgac  28

<210> SEQ ID NO 16
<211> LENGTH: 33
<212> TYPE: DNA
<213> ORGANISM: Solenopsis Invicta Virus

<400> SEQUENCE: 16
aatggaagaa gacacttcga tgtggcacga ctc  33

<210> SEQ ID NO 17
<211> LENGTH: 34
<212> TYPE: DNA
<213> ORGANISM: Solenopsis Invicta Virus

<400> SEQUENCE: 17

```
<210> SEQ ID NO 18
<211> LENGTH: 20
<212> TYPE: DNA
<213> ORGANISM: Solenopsis Invicta Virus

<400> SEQUENCE: 18
cattgggttg gttaaatatg                                              20

<210> SEQ ID NO 19
<211> LENGTH: 25
<212> TYPE: DNA
<213> ORGANISM: Solenopsis Invicta Virus

<400> SEQUENCE: 19
cacaactggt tgggttcgag gtttg                                        25

<210> SEQ ID NO 20
<211> LENGTH: 21
<212> TYPE: DNA
<213> ORGANISM: Solenopsis Invicta Virus

<400> SEQUENCE: 20
tgacttacct acgccacttt c                                            21

<210> SEQ ID NO 21
<211> LENGTH: 2864
<212> TYPE: DNA
<213> ORGANISM: Solenopsis Invicta Virus
<300> PUBLICATION INFORMATION:
<301> AUTHORS: Steven Valles and Charles A. Strong
<302> TITLE: Solenopsis invicta virus-1A (SINV-1A): Distinct species or
      genotype of SINV-1
<303> JOURNAL: Journal of Invertebrate Pathology
<304> VOLUME: 88
<306> PAGES: 232-237
<307> DATE: 2005-03-25
<300> PUBLICATION INFORMATION:
<308> DATABASE ACCESSION NUMBER: GenBank
<309> DATABASE ENTRY DATE: 2005-07-25
<313> RELEVANT RESIDUES: (1)..(2864)

<400> SEQUENCE: 21
taatctacct acaataaaga atatcccata tagacaatta ccccaaacta ataccaatgc    60
aaagaagatt gaaatagatc gaaaattggc taaattagaa aagaagaacc cttccgctta   120
taaatatata actaatattt tagatatacg gccggccacc atgcagaccg catggggcac   180
tccatcacaa ttattaatta aggatgtttt agatttagca ccggtattta acgaacttca   240
agcagtatta tctgaagtgt gtggatcaat taggaaccga gacttttcgt tgaggccttt   300
atataaagta cgcatacatg ctatgcaaga cttaatcaat gattccttaa agaggatgtt   360
tgatagatat gaggccctgg acgagacgga tcttatgagt gaagacacac cagataatgc   420
tttcccaact atggttttat atttggattc ccttaagaaa attaataagt caaaatcaga   480
gtatgtggag atgcaattgg atgcctatga tgcacgagat attgatggta tgttaaatgc   540
atataatcaa ttgaaagagt ttaatcacca tacagcaaga aaggagatgg tgtcaatgat   600
gcatctgggt tatcaatatt cccaacggcg gcaccgacga gatgtaacag cagcaagagc   660
catagcagat acaatacttg tagatgaacg cgatgcaaca atgcaagtcc aagcagaagt   720
aggaggacag ggtcttatta ctgacatagc ctctaccgtt tcggcggtgg cgggtgcagt   780
```

```
cagtggtatc ccggttatag gagaaattgc atctacagtt ggttgggttt ctgatatagt      840
tggaggaatt tcctccatct ttggatggtc tcgaccaaat gacatggaaa aagtaacatc      900
tttggcaaac gttcctggca agtattattc tcacgtaaaa gcagtagata atagtgtagc      960
tttagctttg agtaatgaga acgaacttct cccgcttagt gacatctttc cctcagcagt     1020
agatgagatg gatttggcat acgtgtgtgc caaccccgga gtgaaggagg tcattacatg     1080
gtcgaagaca gatcccatga ataagacttt agcattaatg gaagtaggat acctagtttt     1140
taatagatat caggataagg caatagattg tgatagtgaa cccactccat acaacatttg     1200
taataaagat ttaattaaac caaatgggaa tattattttg agccctgggg atctggtgca     1260
gatgaaaggt agcctggctg cgacaatctt ggacactgtt ccatgcgaat acgtgtctca     1320
gttgtttcag tattgcgtg ctacaatttg ctttaagatt tccgtggtga aaactggttt       1380
ccatacagga cgtttggaga ttttctttga ccctggtgag tatcttacta atcctaaggc     1440
ggattggcat aattatgttg atctttcggc ttatgataag gtggatactg caaattctta     1500
caaatatatt ttagatttaa cgaatgattc agaaattacc attagagtac catttattag     1560
tgataggtta gctttaagca aatcggtgc caatagttat ggtgaggatg gtgtgatggg      1620
acccccaaat ttgaacgata ttttcgattc aatgattggg tctctgatca tcaggccgct     1680
cacgaggctt atggcgccag atacagtttc agatcaggtt aaaatagtaa tttgaaaatg     1740
ggctgaagat gtgcagctcc ttgttcctaa agaatcaaat caactcgaaa tcgttccata     1800
cgagtttgag cgaacaccag gtttgacatg caagaaacaa aagatttctg atcaagatat     1860
gaaggtgttt attgcgcatt gggaaaaaga tggtcaatgg gtttgtactt cagacccaac     1920
cacaagcatg gtcttttcat ggggacaata tcccttatgt gagaccagaa atgctacgat     1980
gcagataaac atttctaatg aagcttcagg aaatagtatt gatattttcc aggataataa     2040
tgcaggtgta agtccaaacg cagttatggg gaaaattgca ggtgaacgtt tagttaacct     2100
acgaccatta ttgcgatgct ttcgttcctt gggtggcata acgctggatc gggcaggtca     2160
aatcctgtct gagagagtgt attggcatta taaggattac gttagcatac tttcatacct     2220
gtatcgattt tctagaggag gatatcgcta caagtttttt gcagatgaca acgaacaagg     2280
acaagtcatg tcaacgcttg ttaaaaatta ccacaaggac catgctacaa gcactggtcc     2340
ttcccatatg acttacaata atctcaaccc cgtacacgaa attatgatcc catattattc     2400
tcaatatagg aaaattccaa tttcaggcga agtagaatta attaaaggta agattcagac     2460
acctgtagaa aagggcatta aaggtgagct ttatcgctca ggaaatgatg acctgacata     2520
cgggtggatc gttggatcgc cccaacttta tgttggagca gctcaacggt ggagttgttg     2580
gacagtaaca aagccaacac aactaggcac taaggaaact taatgatag taaatttgc      2640 tcttcaggga cagtcaaatc tctggagttc ggttttattc ttcaaaattc ttttaaaaca     2700
gaggacgtat gtggaatggc gagcactatt gttcggattc acgattttga gaaaactcac     2760
tagatggagg ctcttgatct attagcagtc tgagataatc taacgatttc acatgcgaac     2820
gcatattcaa gtaaattaaa ttaagaaaaa aaaaaaaaa aaaa                       2864
```

<210> SEQ ID NO 22
<211> LENGTH: 30
<212> TYPE: DNA
<213> ORGANISM: Solenopsis Invicta Virus

<400> SEQUENCE: 22

```
gcgataggtt agctttaagt acaattggtg                                        30
```

-continued

<210> SEQ ID NO 23
<211> LENGTH: 25
<212> TYPE: DNA
<213> ORGANISM: Solenopsis Invicta Virus

<400> SEQUENCE: 23
tcccaatgtg caataaacac cttca                                                25

<210> SEQ ID NO 24
<211> LENGTH: 29
<212> TYPE: DNA
<213> ORGANISM: Solenopsis Invicta Virus

<400> SEQUENCE: 24
cgccttagga ttcgttagat actcacccg                                            29

<210> SEQ ID NO 25
<211> LENGTH: 22
<212> TYPE: DNA
<213> ORGANISM: Solenopsis Invicta Virus

<400> SEQUENCE: 25
cttgatcggg caggacaaat tc                                                   22

<210> SEQ ID NO 26
<211> LENGTH: 22
<212> TYPE: DNA
<213> ORGANISM: Solenopsis Invicta Virus

<400> SEQUENCE: 26
gaacgctgat aaccaatgag cc                                                   22

<210> SEQ ID NO 27
<211> LENGTH: 34
<212> TYPE: DNA
<213> ORGANISM: Solenopsis Invicta Virus

<400> SEQUENCE: 27
cactccatac aacatttgta ataaagattt aatt                                      34

<210> SEQ ID NO 28
<211> LENGTH: 25
<212> TYPE: DNA
<213> ORGANISM: Solenopsis Invicta Virus

<400> SEQUENCE: 28
ccaatactga acaactgag acacg                                                 25

<210> SEQ ID NO 29
<211> LENGTH: 25
<212> TYPE: DNA
<213> ORGANISM: Solenopsis Invicta Virus

<400> SEQUENCE: 29
ccaatactga acaactgag acacg                                                 25

<210> SEQ ID NO 30
<211> LENGTH: 32
<212> TYPE: DNA
<213> ORGANISM: Solenopsis Invicta Virus

<400> SEQUENCE: 30

```
cttaattgta atttacttga atatgcgttt gc                                    32
```

<210> SEQ ID NO 31
<211> LENGTH: 27
<212> TYPE: DNA
<213> ORGANISM: Solenopsis Invicta Virus

<400> SEQUENCE: 31

```
gtatctaacg aatcctaagg cggattg                                          27
```

<210> SEQ ID NO 32
<211> LENGTH: 27
<212> TYPE: DNA
<213> ORGANISM: Solenopsis Invicta Virus

<400> SEQUENCE: 32

```
caatccgcct taggattcgt tagatac                                          27
```

<210> SEQ ID NO 33
<211> LENGTH: 27
<212> TYPE: DNA
<213> ORGANISM: Solenopsis Invicta Virus

<400> SEQUENCE: 33

```
cggatcttat gagtgaagac acaccag                                          27
```

<210> SEQ ID NO 34
<211> LENGTH: 21
<212> TYPE: DNA
<213> ORGANISM: Solenopsis Invicta Virus

<400> SEQUENCE: 34

```
caacctctgc ttcccacgca c                                                21
```

<210> SEQ ID NO 35
<211> LENGTH: 26
<212> TYPE: DNA
<213> ORGANISM: Solenopsis Invicta Virus

<400> SEQUENCE: 35

```
gatggtctcg accaaatgat atggag                                           26
```

<210> SEQ ID NO 36
<211> LENGTH: 31
<212> TYPE: DNA
<213> ORGANISM: Solenopsis Invicta Virus

<400> SEQUENCE: 36

```
atgaagatat gaaggtgttt attgcacatt g                                     31
```

<210> SEQ ID NO 37
<211> LENGTH: 24
<212> TYPE: DNA
<213> ORGANISM: Solenopsis Invicta Virus

<400> SEQUENCE: 37

```
cacataaggg atattgtccc catg                                             24
```

<210> SEQ ID NO 38
<211> LENGTH: 24
<212> TYPE: DNA
<213> ORGANISM: Solenopsis Invicta Virus

<400> SEQUENCE: 38

-continued tggacgagac ggatcttatg agtg 24

<210> SEQ ID NO 39
<211> LENGTH: 25
<212> TYPE: DNA
<213> ORGANISM: Solenopsis Invicta Virus

<400> SEQUENCE: 39
gctgtcaacg atacgctacg taacg 25

<210> SEQ ID NO 40
<211> LENGTH: 603
<212> TYPE: DNA
<213> ORGANISM: Solenopsis Invicta Virus

<400> SEQUENCE: 40
tgtctgaaag agtgtattgg aaccacaaag attatgttag catactctca tatctgtatc 60
gtttttccag agggggatat cgttacaaat tcttcgcaga cgataacgga cagggacaag 120
tcatgtcaac gcttgtcaaa aattactaca aggaccatgc aacaagtact ggtccatccc 180
atatgactta caataatatt aatcccgtac atgaaattat gatcccatat tactctcaat 240
ataggaaaat cccaatttca ggcgaagtag aattgattaa aggtaagatt caaactcccg 300
tagaaaaggg cattaaaggt gagctttatc gctcaggaaa tgatgaccta acctatgggt 360
ggatcgttgg atcgccccag ctttatgttg gagcggctca acgatggagt tgttggacag 420
taacaaagcc aacacaacta gtcactaagg aaacttaatg gatagtaaat tttgctcttc 480
aaagacagtc aaatctttgg agttcggttt tattcttcaa aattctttta aaacagagga 540
tgcatagtta atggcgagca ctatcgtccg gaatgacacc tttgagaaaa ctcactagat 600
gga 603

<210> SEQ ID NO 41
<211> LENGTH: 603
<212> TYPE: DNA
<213> ORGANISM: Solenopsis Invicta Virus

<400> SEQUENCE: 41
tgtctgaaag agtgtattgg aaccacaaag attatgttag catactctca tatctgtatc 60
gtttttccag agggggatat cgttacaaat tcttcgcaga tgataacgaa cagggacaag 120
tcatgtcaac gcttgtcaaa aattactaca aggaccatgc aacaagtact ggtccatccc 180
atatgactta caataatatt aatcccgtac atgaaattat gatcccatat tattctcaat 240
ataggaaaat cccaatttca ggcgaagtag aattaattaa aggtaagatt caaactcccg 300
tagaaaaggg cattaaaggt gagctttatc gctcaggaaa tgatgaccta acctatgggt 360
ggatcgttgg atcgccccag ctttatgttg gagcggctca acgatggagt tgttggacag 420
taacaaagcc aacacaacta gtcactaagg aaacttaatg gatagtaaat tttgctcttc 480
aaagacagtc aaatctttgg agttcggttt tattcttcaa aattctttta aaacagagga 540
tgcatagtta atggcgagca ctatcgtccg gaatgacacc tttgagaaaa ctcactagac 600
gga 603

<210> SEQ ID NO 42
<211> LENGTH: 603
<212> TYPE: DNA
<213> ORGANISM: Solenopsis Invicta Virus -continued

<400> SEQUENCE: 42

```
tgtctgaaag agtgtattgg aatcacaaag attatgttag catactctca tatctgtatc     60
gtttttccag agggggatat cgttacaaat tcttcgcaga cgataacgaa cagggacaag    120
tcatgtcaac gcttgtcaaa aattactaca aggaccatgc aacaagtact ggtccatccc    180
atatgactta caataatatt aatcccgtac atgagattat gatcccatat tattctcaat    240
ataggaaaat cccaatttca ggcgaagtag aattaattaa aggtaagatt caaactcccg    300
tagaaaaggg cattaaaggt gagctttatc gctcaggaaa tgatgaccta acctatgggt    360
ggatcgttgg atcgccccag ctttatgttg gagcggctca acgatggagt tgttggacag    420
taacaaagcc aacacaacta gtcactaagg aaacttaatg gatagtaaat tttgctcttc    480
gaagacagtc aaatctttgg agttcggttt tattcttcaa aattctttta aaacagagga    540
tgcatagtta atggcgagca ctatcgtccg gaatgacacc tttgagaaaa ctcactagat    600
gga                                                                  603
```

<210> SEQ ID NO 43
<211> LENGTH: 603
<212> TYPE: DNA
<213> ORGANISM: Solenopsis Invicta Virus

<400> SEQUENCE: 43

```
tgtctgaaag agtgtattgg aaccacaaag attatgttag catactctca tatctgtatc     60
gtttttccag agggggatat cgttacaaat tcttcgcaga cgataacgaa cagggacaag    120
tcatgtcaac gcttgtcaaa aattactaca aggaccatgc aacaagtact ggtccatccc    180
atatgactta caataatatt aatcccgtac atgaaattat gatcccatat tattctcaat    240
ataggaaaat cccaatttca ggcgaagtag aattaattaa aggtaagatt caaactcccg    300
tagaaaaggg cattaaaggt gagctttatc gctcaggaaa tgatgaccta acctatgggt    360
ggatcgttgg atcgccccag ctttatgttg gagcggctca acgatggagt tgttggacag    420
taacaaagcc aacacaacta gtcactaagg aaacttaatg gatagtaaat tttgctcttc    480
aaagacagtc aaatctttgg agttcggttt tattcttcaa aattctttta aaacagagga    540
tgcatagtta atggcgagca ctatcgtctg gaatgacacc attgagaaaa ctcactagat    600
gga                                                                  603
```

<210> SEQ ID NO 44
<211> LENGTH: 603
<212> TYPE: DNA
<213> ORGANISM: Solenopsis Invicta Virus

<400> SEQUENCE: 44

```
tgtctgaaag agtgtattgg aatcacaaag attatgttag catactctca tatctgtatc     60
gtttttccag agggggatat cgttacaaat tcttcgcaga cgataacgaa cagggacaag    120
tcatgtcaac gcttgtcaaa aattactaca aggaccatgc aacaagtact ggtccatccc    180
atatgactta caataatatt aatcccgtac atgagattat gatcccatat tattcccaat    240
ataggaaaat cccaatttca ggcgaagtag aattaattaa aggtaagatt caaactcccg    300
tagaaaaggg cattaaaggt gagctttatc gctcaggaaa tgatgaccta acctatgggt    360
ggatcgttgg atcgccccag ctttatgttg gagcggctca acgatggagt tgttggacag    420
taacaaagcc aacacaacta gtcactaagg aaacttaatg gatagtaaat tttgctcttc    480
aaagacagtc aaatctttgg agttcggttt tattcttcaa aattctttta aaacagagga    540
```

-continued

```
tgcatagtta atggcgagca ctatcgtccg gaatgacacc tttgagaaaa ctcactagat    600
gga                                                                  603

<210> SEQ ID NO 45
<211> LENGTH: 154
<212> TYPE: DNA
<213> ORGANISM: Solenopsis Invicta Virus

<400> SEQUENCE: 45
cactccatac aacatttgta ataaagattt aattaaacca aatgggaata ttgttttgag     60
ccctggggat ctggtgcaga tgaaaggtag cctggctgcg acaattttag acactgttcc    120
atgtgaatac gtgtctcagt tgtttcagta ttgg                                154

<210> SEQ ID NO 46
<211> LENGTH: 154
<212> TYPE: DNA
<213> ORGANISM: Solenopsis Invicta Virus

<400> SEQUENCE: 46
cactccatac aacatttgta ataaagattt aattaaacca aatgggaata tcattttgag     60
ccctggggat ctggtgcaga tgaagggtag cctggctgcg acaattttgg acactgttcc    120
atgtgaatac gtgtctcagt tgtttcagta aagg                                154
```

SOLENOPSIS INVICTA VIRUSES

BACKGROUND OF THE INVENTION

1. Field of the Invention

This invention relates to biological methods and products useful for the control of *Solenopsis invicta*. More specifically, the present invention is directed to novel *Solenopsis invicta* viruses, nucleic acids encoding the novel viruses, biocontrol compositions, and methods of using the viruses and/or biocontrol compositions for control of fire ants.

2. Description of the Related Art

Red imported fire ant, *Solenopsis invicta* (Buren), was first detected in the United States near Mobile, Ala. in the late 1920s (Loding, USDA Insect Pest Surv. Bull., Volume 9, 241, 1929). Since that time, it has spread to encompass more than 128 million hectares, primarily in the southeastern United States (Williams et al., Am. Entomol., Volume 47, 146-159, 2001). Fire ants are known to destroy young citrus trees, growing crops, and germinating seeds. This has an economic impact on agriculture in infested areas. Telephone companies spend substantial amounts of money each year treating their electrical equipment to prevent fire ant invasion because fire ants accumulate at electrical contacts and can short out electrical equipment. Even, farm equipment can be damaged by large fire any mounds. Fire ants also present a danger to wildlife, such as ground nesting birds and animals. Furthermore, fire ants are known to excavate the soil from under roadways causing damage.

Fire ants also pose health care problems to millions of people stung each year-a significant number of which require medical care. Fire ant stings are also blamed for human deaths. Consequently, there is much interest in controlling these troublesome pests.

This interest has resulted in much research and resources being expended through the years to develop reagents and methods for controlling fire ants. While many useful insecticide formulations have resulted from this research, the problems associated with fire ants still exist because the relief gained by insecticide use is only temporary. Once the insecticide pressure is relaxed, fire ant populations invariably repopulate the areas. This reinfestation ability is attributed to the high reproductive capabilities, the efficient foraging behavior, and the ecological adaptability of the ants. While effective for controlling ants in relatively small defined areas, insecticides can create other problems. For example, some insecticides, which are effective at controlling fire ants, can pose a significant threat to the environment, including birds and animals.

Although considerable research effort has been brought to bear against the red imported fire ant, it remains the primary pest ant species in infested areas; initial eradication trials failed, yielding to the wide distribution of pesticide-based control products and a federally imposed quarantine to prevent further spread. Recently, much of the research effort has focused on elucidating basic life processes in an attempt to develop unique control measures, and fostering the development of self-sustaining methods of control, including biocontrol organisms and microbes (Williams et al., Am. Entomol., Volume 49, 150-163, 2003).

A dearth of natural enemies of the red imported fire ant have been found including a neogregarine (Pereira et al., J. Invertebr. Pathology, Volume 81, 45-48, 2002) and a fungus (Pereira et al., J. Invertebr. Pathology, Volume 84, 38-44, 2004).

U.S. Pat. No. 6,660,290 discloses a non-sporulating mycelial stage of an insect-specific parasitic fungi for control of pests with fire ants listed as one of many examples of insects controlled by the biopesticide.

U.S. Pat. Nos. 4,925,663; 5,683,689; 6,254,864; and 6,403,085 disclose a biopesticide effective against fire ants that includes the fungus *Beauveria bassiana*.

There remains a need for biocontrol and/or microbial control agents that eliminate or at least reduce the spread of fire ant colonies using novel pathogens. The present invention described below is directed to novel *Solenopsis invicta* viruses useful for the control of fire ants which are different from prior art pathogens and their uses.

SUMMARY OF THE INVENTION

It is therefore an object of the present invention to provide novel *Solenopsis invicta* virus (SINV) for biocontrol of *Solenopsis invicta*.

A further object of the present invention is to provide a nucleic acid sequence of SINV-1 for production of primers and biocontrol compositions.

A still further object of the present invention is to provide nucleic acid sequence SEQ ID NO 1.

Another object of the present invention is to provide nucleic acid sequence ID NO 21.

Another object of the present invention is to provide a biocontrol method for controlling fire ants that includes applying SINVs to a carrier that is a fire ant food source to form a biocontrol composition which is scattered near a fire ant colony.

Further objects and advantages of the present invention will become apparent from the following description.

BRIEF DESCRIPTION OF THE DRAWINGS

FIGS. 2A-D are drawings showing comparisons of predicted amino acid sequences of nonstructural and structural proteins of SINV-1, picorna-like viruses, and viruses representative of the Picornaviridae and Comoviridae. Alignments are of the conserved regions of the putative helicase (A), cysteine protease (B), RNA-dependent RNA polymerase (RdRp) (C), and capsid protein (D). The numbers on the left indicate the starting amino acids of aligned sequences. Identical residues in at least four of the six virus sequences are shown in the reverse. Sequence motifs shown for the helicase (hel A, hel B, and hel C) and RdRp (I-VIII) correspond to those identified and reviewed by Koonin and Dolja (Crit. Rev. Biochem. Mol. Biol., Volume 28, 375-430, 1993). Asterisks above residues of the protease (B) correspond to the putative catalytic triad, which are considered essential for activity (Koonin and Dolja, 1993, supra; Ryan and Flint, J. Gen. Virol., Volume 78, 699-723, 1997). The last sequence shown (D) represents one of the conserved areas of the putative capsid protein region. The SINV-1 virus sequence exhibited greatest overall identity with acute bee paralysis virus.

FIG. 9 is a graph showing the prevalence of the SINV-1 and SINV-1A in *Solenopsis invicta* fire ant colonies sampled from two field locations in Gainesville, Fla.

FIGS. 10A-10E show SEQ ID NO 1.

FIG. 11 shows the SINV-1A ORF-2 nucleic acid sequence SEQ ID NO 21.

FIG. 12 shows a cloned amplicon (SEQ ID NO 40) of SINV-1 infected fire ants from California that corresponds to a portion of the 3'-proximal open reading frame which encodes the structural proteins of the virus.

FIG. 13 shows a cloned amplicon (SEQ ID NO 41) of SINV-1 infected fire ants from Louisiana that corresponds to a portion of the 3'-proximal open reading frame which encodes the structural proteins of the virus.

FIG. 14 shows a cloned amplicon (SEQ ID NO 42) of SINV-1 infected fire ants from Oklahoma that corresponds to a portion of the 3'-proximal open reading frame which encodes the structural proteins of the virus.

FIG. 15 shows a cloned amplicon (SEQ ID NO 43) of SINV-1 infected fire ants from South Carolina that corresponds to a portion of the 3'-proximal open reading frame which encodes the structural proteins of the virus.

FIG. 16 shows a cloned amplicon (SEQ ID NO 44) of SINV-1 virus infected fire ants from Texas that corresponds to a portion of the 3'-proximal open reading frame which encodes the structural proteins of the virus.

FIG. 17 shows a cloned amplicon (SEQ ID NO 45) of SINV-1A infected fire ants from South Carolina that corresponds to a portion of the 3'-proximal open reading frame which encodes the structural proteins of the virus.

FIG. 18 shows a cloned amplicon (SEQ ID NO 46) of SINV-1A infected fire ants from Texas that corresponds to a portion of the 3'-proximal open reading frame which encodes the structural proteins of the virus.

DETAILED DESCRIPTION OF THE INVENTION

Figure 1A:
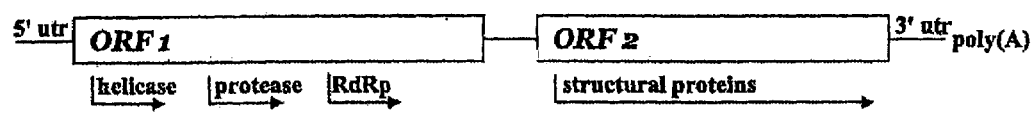
FIG. 1A is a drawing showing a schematic diagram of the *Solenopsis invicta* virus-1 (SINV-1) genome; open reading frames (ORFs) are shown in open boxes. Arrows represent approximate positions of nonstructural and structural proteins in ORFs 1 and 2, respectively.

Although viruses can be important biological control agents against insect populations (Lacey et al., Biol. Comtemp., Volume 21, 230-248, 2001), none have been shown to infect *Solenopsis invicta*. The only report present in the literature was the observation of "virus-like particles" in a *Solenopsis* species from Brazil (Avery et al., Brazil. Fla. Entomol., Volume 60, 17-20, 1977). *Solenopsis invicta* viruses (SINV) represent the first infection of the red imported fire ant by this group of organisms. In the laboratory, SINV causes brood death of an entire colony and infection of healthy colonies (Valles et al., Virology, Volume 328, 151-157, 2004; Valles et al., J. Invert. Path., Volume 88, 232-237, 2005; both references herein incorporated in their entirety).

SINV particles are isometric with a diameter of about 31 nm. They have a monopartite, bicistronic, single-stranded RNA genome. To date, several SINV viruses have been isolated. SINV-1 is composed of about 8026 nucleotides. The genome size was confirmed by Northern analysis in which a band was observed at about 8.4 kb. ORFs 1 and 2 were found to be homologous to nonstructural and structural proteins, respectively, of well-characterized picorna-like viruses (Ghosh et al, J. Gen. Virol., Volume 80, 1541-1549, 1999; Govan et al., Virology, Volume 277, 457-463, 2000; Leat et al., J. Gen. Virol., Volume 81, 2111-2119, 2000).

SINV-1 ORF-1 amino acid sequence was aligned with acute bee paralysis virus (ABPV), sacbrood virus (SBV), black queen cell virus (BQCV), cow pea mosaic virus (CPMV), and hepatitis A virus (HAV) using the Vecto NTI alignment sotware with ClustalW algorithm (InforMax, Inc., Bethesda, Md.) (FIGS. 2 and 10). Alignment of ORFs encoding nonstructural proteins with SINV-1 ORF 1 showed identities ranging from 10% (SBV, CPMV, HAV) to 30% (ABPV). The alignments also revealed sequence motifs for a helicase, protease, and RNA-dependent RNA polymerase (RdRp), characteristic of Picornaviridae, Comoviridae, Sequiviridae, and Caliciviridae (Koonin and Dolja, Crit. Rev. Biochem. Mol. Biol., Volume 28, 375-430, 1993). Amino acid positions 23-144 exhibited similarity to the helicase. The consensus sequence for the RNA helicase, $Gx_4GK$ (Gorbalenya et al., FEBS Lett., Volume 262 145-148, 1990), was found in the predicted ORF1 of SINV-1 at amino acids 34-40. Amino acids 663-823 showed similarity to the cysteine protease of picorna-, picorna-like-, sequi-, and comoviruses. Amino acids thought to form the catalytic triad of the protease, $H^{667}$, $E^{710}$, and $C^{802}$ were present in this region of the SINV-1 (Koonin and Dolja, 1993, supra;

Ryan and Flint, J. Gen. Virol., Volume 78, 699-723, 1997). Furthermore, the consensus GxCG sequence motif was present at amino acids 800-803. Lastly, ORF1 of SINV-1 contained sequence with similarity to RdRp (amino acids 1052-1327). According to Koonin and Dolja (1993, supra) all-positive-strand RNA viruses encode the RdRp and comparative analysis revealed that they possess eight common sequence motifs (Koonin, J. Gen. Virol., Volume 72, 2197-2206, 1991). All eight of these motifs were present in SINV-1. Further, sequence motifs IV, V, and VI were reported to be unequivocally conserved throughout this class of viruses, exhibiting six invariant amino acid residues (Koonin and Dolja, 1993, supra). These "core" RdRp motifs were shown by site-directed mutagenesis to be crucial to the activity of the enzyme (Sankar and Porter, I. J. Biol. Chem., Volume 267, 10168-10176, 1992). The SINV-1 possesses all six of these characteristic residues, $D^{1130}$, $D^{1135}$ (motif IV), $G^{1190}$, $T^{1194}$ (motif V), and $D^{1248}$, $D^{1249}$ (motif VI). Thus, these data strongly support the conclusion that SINV-1 is a single-stranded positive RNA virus.

During elucidation of the genome of SINV-1, a nucleotide sequence, similar to but distinct from SINV-1, was discovered. The sequence, SINV-1A, is homologous to SINV-1 ORF 2, i.e., structural proteins, of picorna-like insect viruses with highly significant identity to SINV-1. This suggests that SNV-1A is a distinct, closely related species or a genotype of SINV-1 (FIG. 11 and SEQ ID NO 21).

SINV-1A is sufficiently similar to SINV-1 to occasionally result in amplification even in cases where oligonucleotide mismatches were present. SINV-1A is a compilation of contiguous fragments that do not match the SINV-1 sequence perfectly.

The nucleotide sequence of the 3'-end (structural proteins) of SINV-1 and SINV-1A exhibit about 89.9% nucleotide identity and about 97% amino acid identity of the translated 3' proximal ORF.

SINV-1 and SINV-1A infect S. invicta in the same geographic locations (sympatry). S. invicta has 2 distinct social forms, monogyne and polygyne, and these differences were shown recently to have a genetic basis (Krieger and Ross, Science, Volume 295, 328-332, 2002). Monogyne S. invicta is characterized as having a single fertile queen and polygyne S. invicta has multiple fertile queens. Both viruses infect both social forms. Dual infections with SINV-1 and SINV-1A were found in both monogyne and polygyne nests. Social form-specific pathogen infectivity has been reported previously in S. invicta. Oi et al. (Environ. Entomol., Volume 33, 340-345, 2004) showed that infection of North American S. invicta with the microsporidian Thelohania solenopsis, was restricted to the polygyne social form.

Other SINV viruses have been discovered in fire ant colonies in California, Louisiana, South Carolina, Texas, and Florida. SEQ ID NOs 40-46 (FIGS. 12-18) represent cloned amplicons from these virus-infected ants. The cloned amplicons were generated with oligonucleotide primers p114 (SEQ ID NO 25) and p116 (SEQ ID NO 26) for SINV-1 and p117 (SEQ ID NO 27) and p118 (SEQ ID NO 28) for SINV-1A using RT-PCR. The areas amplified correspond to a portion of the 3'-proximal open reading frame which encodes the structural proteins of the virus. Each primer set is specific to each virus or genotype.

SINV-1 and SINV-1A were found to infect all fire ant castes. The viruses are transmissible by simply feeding uninfected ants a homogenate prepared from SINV-1- and/or SINV-1A-infected individuals. The viruses were present in field populations of S. invicta from several locations in Florida. Nests from some areas were devoid of infection, but in some locations infection rates were as high as about 88%.

The present invention provides nucleic acids encoding for SINV-1 as set forth in SEQ ID NO 1 (GenBank Accession NO. AY634314; herein incorporated by reference) and FIGS. 10A-10E. The invention also provides nucleic acid sequences (SEQ ID NO 2-20) capable of selectively hybridizing DNA, RNA, and cDNA sequences which can be derived from SEQ ID NO 1. To isolate SINV-1, RNA from fire ants, collected from a fire ant mound, was extracted from about 20-50 workers using TRIZOL reagent according to the manufacturer's directions (Invitrogen, Carlsbad, Calif.).

The present invention also provides a nucleic acid encoding ORF2 gene for SINV-1A as set forth in SEQ ID NO 21. The invention also provides nucleic acid sequences 2, 3, and 22-39 which are capable of selectively hybridizing DNA, RNA, and cDNA sequences which can be derived from SEQ ID NO 21.

The present invention further provides nucleic acid encoding 3'-proximal open reading frames for other SINV viruses infecting ants from other several different regions of the United States.

With the primers of the present invention, one of ordinary skill in the art could readily identify SINV viruses of the present invention.

For purposes of the present invention, the term "fire ant" and "Solenopsis invicta" are used interchangeably to describe the common red fire ant, originating in South America, but now commonly found in the United States, and Puerto Rico. The term fire ant also is used to describe black fire ants and other hybrid fire ants or other ants that are infected by the viruses of the present invention.

For purposes of the present invention, the term "isolated" is defined as separated from other viruses found in naturally occurring organisms.

For purposes of the present invention, the term "composition" is used to describe a composition which contains the virus of the presently claimed invention, optionally a carrier and optionally a pesticide. The carrier component can be a liquid or a solid material and is an inert, non-repellent carrier for delivering the composition to a desired site. Liquids suitable as carriers include water, and any liquid which will not affect the viability of the viruses of the present invention. Solid carriers can be anything which the fire ant will feed on. Non-limiting examples of solid carriers of the present invention include materials such as corn cob grits, extruded corn pellets, boiled egg yolks, and frozen insects such as crickets.

Optional toxicants include Chlorfenapyr, Imidacloprid, Fipronil, Hydramethylnon, Sulfluramid, Hexaflumuron, Pyriproxyfen, methoprene, lufenuron, dimilin, Chlorpyrifos, and their active derivatives, Neem, azadiractin, boric acid based, etc. The toxicant acts as a stressor which may be required to initiate viral replication which in turn results in brood death in the fire ant colony.

The term "effective amount" or "amount effective for" as used herein means that minimum amount of a virus composition needed to at least reduce, or substantially eradicate fire ants in a fire ant colony when compared to the same colony or other colony which is untreated. The precise amount needed will vary in accordance with the particular virus composition used; the colony to be treated; the environment in which the colony is located. The exact amount of virus composition needed can easily be determined by one having ordinary skill in the art given the teachings of the present specification. The examples herein show typical concentrations which will be needed to at least reduce the number of fire ants in a colony.

In the present method of using the viruses of the present invention, to reduce or eradicate a population of fire ants, the present compositions are delivered to the fire ants by spreading the composition at or near the fire ant colonies. The amount of composition used is an effective amount for producing the intended result, whether to reduce or eradicate the population of fire ants. The composition is prepared by homogenizing approximately 300 workers from an SINV infected colony in an equal volume of water and placing the resulting homogenate on a carrier.

The following examples are intended only to further illustrate the invention and are not intended to limit the scope of the invention as defined by the claims.

EXAMPLE 1

A one-step reverse transcriptase polymerase chain reaction (RT-PCR) was used to identify SINV-1-infected *S. invicta* ants. A 20 ml scintillation vial was plunged into a fire ant mound in the field for several minutes to collect a sample of the worker caste. The ants were returned to the laboratory and RNA was extracted from about 20-50 workers using TRIZOL reagent according to the manufacturer's directions (Invitrogen, Carlsbad, Calif.). cDNA was synthesized and subsequently amplified using the One-Step RT-PCR kit (Invitrogen) with oligonucleotide primers p62-SEQ ID NO 25 and p63-SEQ ID NO 26 (Table 1). Samples were considered positive for the virus when a visible amplicon (about 327 nucleotides) was present after separation on about a 1.2% agarose gel stained with ethidium bromide. RT-PCR was conducted in a PTC 100 thermal cycler (MJ Research, Waltham, Mass.) under the following optimized temperature regime:

1 cycle at about 45° C. for about 30 minutes;
1 cycle at about 94° C. for about 2 minutes;
35 cycles at about 94° C. for about 15 seconds;
1 cycle at about 55° C. for about 15 seconds;
1 cycle at about 68° C. for about 30 seconds; and
a final elongation step of about 68° C. for about 5 minutes.

SINV-1 was purified for electron microscopy by the method described by Ghosh et al. (J. Gen. Virol., Volume 80, 1541-1549, 1999). Briefly, approximately 0.5 grams of a mixture of workers and brood were homogenized in about 5 ml of NT buffer (Tris-HCl, pH about 7.4, approximately 10 mM NaCl) using a Potter-Elvehjem Teflon pestle and glass mortar. The mixture was clarified by centrifugation at about 1000×g for about 10 minutes in an L8-70M ultracentrifuge (Beckman, Palo Alto, Calif.). The supernatant was extracted with an equal volume of 1,1,2-trichlortrifluoroethane before the aqueous phase was layered onto a discontinuous CsCl gradient (about 1.2 and about 1.5 g/ml) which was centrifuged at about 270,000×g for about 1 hour in an SW60 rotor. Two whitish bands visible near the interface were removed by suction and desalted. The sample was negatively stained with about 2% phosphotungstic acid, about pH 7, and examined with a Hitachi H-600 transmission electron microscope (Hitachi, Pleasanton, Calif.) at an accelerating voltage of about 75 kV. Uninfected worker ants were prepared and examined in the same manner and served as controls.

A portion of the SINV-1 genome was identified from an expression library produced from a monogyne *S. invicta* colony collected in Gainesville, Fla. This contiguous 1780-nucleotide fragment exhibited significant identity with the acute bee paralysis virus and was comprised of clones 14D5, 3F6, and 24C10 (Table 2). From this fragment, a series of 5'RACE reactions were conducted to obtain the upstream sequence of the SINV-1 genome using the 5'RACE system (Invitrogen). cDNA was synthesized with a gene-specific oligonucleotide primer (GSP) from total RNA, the RNA template was degraded with RNase, and the cDNA purified. The 3' end of the cDNA was polycytidylated with terminal deoxynucleotidyl transferase and dCTP. The tailed cDNA was then amplified with a second, upstream GSP and an abridged anchor primer.

Six 5' RACE reactions were necessary to obtain the entire SINV-1 genome. Anticipating the potential need to remove the VPg often covalently attached to the 5' end of insect picorna-like viruses (Christian and Scotti, In: The Insect Viruses, Plenum Publishing Corporation, New York, 301-336, 1998), 50 µg of total RNA prepared from SINV-1 infected ants was digested with about 600 µg/ml proteinase K for approximately 1 hour at about 37° C. The digested RNA was purified by acidic phenol/chloroform/isoamyl alcohol extraction. cDNA synthesis was conducted for about 50 minutes at about 45° C. with approximately 2.5 µg of total RNA using oligonucleotide primers p134-SEQ ID NO 5, p138-SEQ ID NO 7, p138-SEQ ID NO 9, p157-SEQ ID NO 13, p162-SEQ ID NO 14, and p274-SEQ ID NO 20 (See FIGS. 1B, p3 to p8), respectively. After cDNA synthesis, PCR was conducted with an abridged anchor primer and p135-SEQ ID NO 6, p140-SEQ ID NO 11, p154-SEQ ID NO 12, p161-SEQ ID NO 29, and p273-SEQ ID NO 19, respectively. PCR was conducted using the following temperature regime:

1 cycle at about 94° C. for about 2 minutes;
35 cycles of about 94° C. for about 15 seconds;
1 cycle at about 68° C. for about 5 minutes; and
followed by a final elongation step of about 68° C. for about 5 minutes.

Gel-purified amplicons were ligated into pCR4-TOPO vector, transformed into TOP10 competent cells (Invitrogen), and sequenced by the Interdisciplinary Center for Biotechnology Research (University of Florida).

A single 3' RACE reaction was conducted with the GeneRacer kit (Invitrogen). cDNA was synthesized from about 1 µg total RNA purified from SINV-1-infected workers and brood using the GeneRacer Oligo dT primer p113-SEQ ID NO 4 and the GeneRacer 3' primer. Amplicons were cloned and sequenced as described for the 5' RACE.

Northern analysis was conducted to determine the genome size following the general procedure of Sambrook and Russell (Molecular Cloning, Cold Spring Harbor Laboratory Press, Cold Spring Harbor, N.Y., 2001). Membranes were blotted with approximately 6 µg of total RNA from SINV-1-infected and -uninfected fire ant colonies. The approximately 327-nucleotide probe was synthesized using oligonucleotide primers p62-SEQ ID NO 2 and p63-SEQ ID NO 3 (Table 1) and a clone from the 3' end of the genome as template (genomic region 6246 to 6572).

Figure 1B:
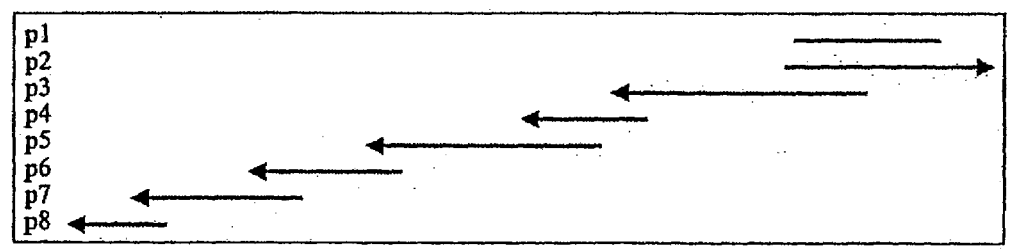
FIG. 1B is a drawing showing a representation of the cloning strategy for the SINV-1 genome. Each line represents a cDNA fragment of the SINV-1 genome. The horizontal axis approximates corresponding positions in the genome diagram, p1, contiguous fragment obtained from the fire ant expression library; p2, 3'RACE; p3-p8, successive 5'RACE reactions.

The genome of SINV-1 was constructed by compiling sequences from a series of six successive 5' RACE reactions, one 3' RACE reaction, and the sequences of three cDNA clones from a fire ant expression library (FIG. 1). The SINV-1 genome, SEQ ID NO 1, was found to be 8026-nucleotides long, excluding the poly(A) tail present on the 3' end (GenBank Accession number AY634314). This genome size was consistent with the largest species (approximately 8.4 kb) produced by Northern analysis of RNA extracted from SINV-1-infected fire ants (data not shown). No hybridization was observed in RNA extracted from uninfected ants.

Typical of Picornaviridae, the genome sequence was A/U rich (approximately 32.9% A, 28.2% U, 18.3% C, and 20.5% G). Analysis of the genome revealed two large open reading frames (ORFs) in the sense orientation (within frame) with an untranslated region (UTR) at each end and between the two ORFs. The 5' proximal ORF (ORF1) commenced at the first start AUG codon present at nucleotide position 28 and ended at a UAA stop codon at nucleotide 4218, which encoded a predicted product of approximately 160,327 Da. The 3' proximal ORF (ORF2), commenced at nucleotide position 4390 (AUG start codon), terminated at nucleotide position 7803 (UAA stop codon), and encoded a predicted product of approximately 127,683 Da. No large ORFs were found in the inverse orientation, suggesting that the SINV-1 genome was a positive-strand RNA virus. The 5', 3', and intergenic UTRs were comprised of about 27,223 and 171 nucleotides, respectively. BLAST analysis (Altschul et al., Nucleic Acids Research, Volume 25, 3389-3402, 1997) of ORFs 1 and 2 revealed identity to nonstructural and structural proteins, respectively, from picorna-like viruses. ORF1 of SINV-1 genome was found to exhibit the characterisitic helicase, protease, and RNA-dependent RNA polymerase (RdRp) sequence motifs ascribed to Picornaviridae (FIG. 2; Koonin and Dolja, 1993, supra). Although ORF2 exhibited homology to structural proteins in the Picornaviridae, the sequence identity was less well conserved as in the nonstructural proteins of ORF1

Figure 3:
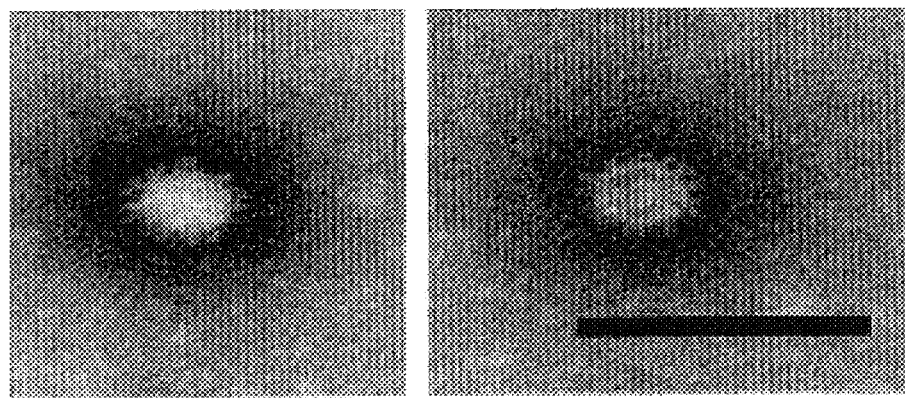
FIG. 3 is an electron micrograph of a particle believed to be SINV-1. The preparation was isolated from SINV-1-infected fire ants. Scale bar represents 100 nm.

Electron microscopic examination of negatively stained samples from SINV-1-infected fire ants revealed particles that were consistent with Picornaviridae (FIG. 3). Isometric particles with a diameter of approximately 31 nm were observed exclusively in preparations from SINV-1-infected fire ants; no corresponding particles were observed in samples prepared from uninfected fire ants.

TABLE 1

Oligonucleotide primers.

| Oligonucleotide Designation | Oligonucleotide (5' → 3') |
|---|---|
| p62 | GGAAGTCATTACGTGGTCGAAAACG SEQ ID 2 |
| p63 | CGTCCTGTATGAAAACCGGTCTTT-ACCACAGAAATCTTA SEQ ID NO 3 |
| p113 | GGAAGTCATTACGTGGTCGAAAAC SEQ ID NO 4 |
| p134 | CCAAGCTGCCCTTCATCTGCACCA-GATC SEQ ID NO 5 |
| p135 | TTCATCTGCACCAGATCTCCAGGG-CTC SEQ ID NO 6 |
| p136 | CAATGATTCAGCAGAAATGGTTAT-CC SEQ ID NO 7 |
| p137 | GTCACATCACGTCGGTGTCGT SEQ ID NO 8 |
| p138 | TCTGCCTTAAAGTATTGATG SEQ ID NO 9 |
| p139 | GTCTCCTGGCAAGGAATACTGTCT-GATGGCTGG SEQ ID NO 10 |
| p140 | GGAAGAGCGACGCGAGGTTGTTCA-ACATC SEQ ID NO 11 |
| p154 | CGCATCAACTTTCTCAATGGGTCG-TCGCTCA SEQ ID NO 12 |
| p157 | CAGTGATACTAGCAATCTGAATA SEQ ID NO 13 |
| p162 | CTATCTAAATGTTGGGAATATC SEQ ID NO 14 |
| p164 | CACCGGATGTTGTGGCCTCCAGAA-TGAC SEQ ID NO 15 |
| p165 | AATGGAAGAAGACACTTCGATGTG-GCACGACTC SEQ ID NO 16 |
| p177 | GAATCGTGCCACATCGAAGTGTCT-TCTTCCATTG SEQ ID NO 17 |

TABLE 1-continued

Oligonucleotide primers.

| Oligonucleotide Designation | Oligonucleotide (5' → 3') |
|---|---|
| p180 | CATTGGGTTGGTTAAATATG SEQ ID NO 18 |
| p273 | CACAACTGGTTGGGTTCGAGGT-TTG SEQ ID NO 19 |
| p274 | TGACTTACCTACGCCACTTTC SEQ ID NO 20 |

TABLE 2

Expression library clones exhibiting homology to viruses after BLAST analysis.

| Clone | BLAST Match | Accession no. | Score |
|---|---|---|---|
| 3B4 | Finkel-Biskis-Reilly murine Sarcoma virus | NP032016 | $3 \times 10^{-22}$ |
| 3F6 | Capsid protein, acute bee paralysis virus | AAL05914 | $1 \times 10^{-17}$ |
| 11F1 | Capsid polyprotein, *Drosophila C* virus | NP044946 | $4 \times 10^{-16}$ |
| 12G12 | Noncapsid protein, *Urochloa hoja blanca* virus | AAB58302 | $5 \times 10^{-12}$ |
| 14D5 | Capsid protein, acute bee paralysis virus | AAK15543 | $1 \times 10^{-26}$ |
| 16A4 | Protein P1, *Acyrthosiphum pisum* virus | NP620557 | $5 \times 10^{-4}$ |
| 18F8 | Polyprotein, sacbrood virus | NP049374 | 5.9 |
| 24C10 | Capsid protein, acute bee paralysis virus | AAL05915 | $2 \times 10^{-13}$ |

EXAMPLE 2

A field survey was conducted to examine the extent of SINV-1 infection among *S. invicta* nests from locations around Florida. Nests were sampled from Gainesville (n=72), Newberry (n=11), LaCrosse (n=9), McIntosh (n=9), Fort Pierce (n=6), Orlando (n=4), Okahumpka (n=4), Ocala (n=4), Canoe Creek (n=4), Fort Drum (n=4), Cedar Key (n=11), Otter Creek (n=10), Bronson (n=9), and Perry (n=11). Samples of workers were retrieved from the field and treated as described above in Example 1. Primer pairs p62/p63 (SEQ ID NO 2/3), p136/p137 (SEQ ID NO 7/8), or p164/p165 (SEQ ID NO 15/16) were used in an RT-PCR reaction to determine the presence of SINV-1 infection (Table 1 above).

Experiments were conducted to determine if the virus was infecting all caste members. Samples of workers were taken from ant nests from areas in Gainesville, Fla. and examined for infection by RT-PCR using primer pairs p62-SEQ ID NO 2/63-SEQ ID NO 26, p136-SEQ ID NO 7/137-SEQ ID NO 8, or p164-SEQ ID NO 15/p165-SEQ ID NO 16 (Table 1 above and Table 4 below). Nests determined to be infected were revisited on the same day, and samples of queens, workers, early instars ($1^{st}$ and $2^{nd}$), late instars ($3^{rd}$ and $4^{th}$), pupae, sexual pupae, and male and female alates were directly taken from the field. Queens were placed separately into 1.5 ml microcentrifuge tubes and held at about 30° C. for about 24 hours to obtain a sample of eggs. All samples were analyzed for infection by RT-PCR.

The PCR analytic survey for the SINV-1 virus from extracts of *S. invicta* collected around Florida revealed a pattern of fairly widespread distribution (Table 3). Among about 168 nests surveyed, infection rates among different sites ranged from about 0% to about 87.5% with a mean of about 22.9% (SD=26.3) infected. It appears that SINV-1 infects *S. invicta* year round in Florida because it was found from May to January. Although the rate of infection among individuals within SINV-1-infected nests was not determined, it was found that the infection was present in all caste members and developmental stages, including eggs, early ($1^{st}$-$2^{nd}$) and late ($3^{rd}$-$4^{th}$) instars, worker pupae, workers, sexual pupae, alates (male and female) and queens (data not shown).

TABLE 3

Survey of fire ant nests for the presence of the fire ant virus (SINV-1).

| Date | Location (city, state) | Nests Surveyed | Nests with SINV-1 (%) |
|---|---|---|---|
| 14 May | Gainesville, FL | 10 | 20 |
| 12 June | Gainesville, FL | 10 | 30 |
| 21 July | Gainesville, FL | 16 | 87.5 |
| 18-30 September | Gainesville, FL | 28 | 14.3 |
| 7 October | Newberry, FL | 11 | 9.1 |
| 10 October | LaCrosse, FL | 9 | 0 |
| 16 October | McIntosh, FL | 9 | 44 |
| 23 December | Gainesville, FL | 8 | 75 |
| 14 January | Fort Pierce, FL | 6 | 0 |
| 14 January | Orlando, FL | 4 | 0 |
| 14 January | Okahumpka, FL | 4 | 25 |
| 14 January | Ocala, FL | 4 | 50 |
| 14 January | Canoe Creek, FL | 4 | 0 |
| 14 January | Fort Drum, FL | 4 | 0 |
| 22 January | Cedar Key, FL | 11 | 27 |
| 22 January | Otter Creek, FL | 10 | 0 |
| 22 January | Bronson, FL | 9 | 22 |
| 29 January | Perry, FL | 11 | 9.1 |

EXAMPLE 3

To evaluate the transmissibility of the SINV-1, uninfected polygyne nests were identified by RT-PCR, excavated from the field, and parsed into two equivalent fragment colonies comprised of a queen, about 0.25 grams of brood, and about 0.5 grams of workers. Colonies were infected by the method described by Ackey and Beck (J. Insect Physiol., Volume 18, 1901-1914, 1972, herein incorporated by reference). Workers and brood, about 1-5 grams each from an SINV-1-infected colony, were homogenized in an equal volume of water and immediately placed onto boiled chicken egg yolks which are a food source for ants. The food source was placed into one of the fragment colonies for about 3 days. The control was identical except uninfected ants were used. Workers from treated and untreated paired fragment colonies were sampled at about 3, 11, and 18 days after introduction of the treated food source and analyzed for the SINV-1 by RT-PCR.

To determine the duration of SINV-1 infection within a fire ant colony, infected colonies were identified in the field, excavated, and placed into rearing trays with a food source of approximately 3 grams of cooked chicken egg yolks, approximately 15 frozen crickets, 10% sugar water, and a colony cell. Periodically, worker ants were removed and analyzed for infection by RT-PCR. Control colonies, without detectable SINV-1 infection, were removed from the field and treated as the infected colonies.

Individuals from uninfected colonies were infected within about 3 days of providing uninfected fire ants the food source mixed with a homogenate made from SINV-1 infected worker ants. SINV-1 did not appear to infect every individual within the recipient colonies; often several samples had to be evaluated by RT-PCR to detect infection. The infection was detectable for at least 18 days after treatment, indicating sustained infection among recipient colonies.

SINV-1 infection was detectable for at least about 3 months among colonies excavated from the field and held in the laboratory.

EXAMPLE 4

A second nucleotide sequence, similar to SINV-1, was discovered during elucidation of the genome of SINV-1. To obtain cDNA of nucleotide sequence similar to but distinct from SINV-1, approximately 50 µg of total RNA prepared from SINV-1A-infected ants as in example 2 was digested with approximately 600 µg/ml proteinase K for about 1 hour at about 37° C. Fire ants were identified as being infected with SINV-1A with oligonucleotide primers p117 and p118 (Seq. ID nos. 29 and 30). The digested RNA was purified by acidic penol:chloroform:isoamyl alcohol extraction. One-step RT-PCR (Invitrogen) was conducted with primer pairs p62-SEQ ID NO 2 p63-SEQ ID NO 3, p102-SEQ ID NO 24, p191-SEQ ID NO 33; p59-SEQ ID NO 23, p221-SEQ ID NO 35; p188-SEQ ID NO 30 p222-SEQ ID NO 36, p188-SEQ ID NO 30, p189-SEQ ID NO 31, p137-SEQ ID NO 8, and p193-SEQ ID NO 34 (Table 4) using the following temperature regime:

Reverse transcriptase at about 45° C. for about 50 minutes

Denaturation at about 94° C. for about 2 minutes 35 cycles of denaturation at about 94° C. for about 15 seconds Annealing (for individual temperatures see Table X) for about 15 minutes, and Elongation at about 68° C. for about 1.5 minutes Final elongation at about 68° C. for about 5 minutes Gel purified amplicons were ligated in to the pCR4-TOPO vector and transformed into TOP10 competent cells (Invitrogen). Insert-positive clones were sequenced by the Interdisciplinary Center for Biotechnology Research, University of Florida.

A single 3' RACE reaction was conducted with the GeneRacer kit (Invitrogen). cDNA was synthesized from approximately 1 µg total RNA purified from SINV-1A-infected workers and brood using the GeneRacer Oligo(dt) primer. The cDNA was amplified by PCR with oligonucleotide primer p58-SEQ ID NO 22 or p114-SEQ ID NO 25 and the GeneRacer 3'primer. Amplicons were cloned and sequenced as described above.

BLAST comparisons of the nucleotide sequence and predicted amino acid sequence of the 3-proximal ORF and Clustal W-based algorithm alignments were conducted using the Vector NTI alignment software (InforMax, Bethesda, Md.).

The 3'-end of the genome of SINV-1A was constructed by compiling sequences from a series of RT-PCRs and a 3'RACE reaction. The sequence was about 2845 nucleotides in length, excluding the poly(A) tail present on the 3'-end (Accession No. AY831776) (SEQ ID NO 21). The nucleotide sequence was comprised of about 31.7% A, 28.6% U, 17.6% C and 22.1% G. Analysis of the nucleotide sequence revealed one large ORF in the sense orientation with untranslated regions (UTRs) of about 160 and 225 nucleotides at the 5' and 3' ends, respectively. Translation of the ORF commenced at nucleotide position 2620 (UAA stop codon), and encoded a predicted product of approximately 92,076 Da. When the SINV-1 and SINV-1A sequences were compared, the start signal in SINV-1 was further upstream and the corresponding ORF larger compared with SINV-1A. Because the sequences of SINV-1 and SINV-1A were so similar, it is likely that the start site could actually be an internal methoinine and the ORF site begins somewhere further upstream. No large ORFs were found in the inverse orientation. BLAST analyses (Altschul et al., Nucleic Acids Res., Volume 25, 3389-3402, 1997) of the translated ORF revealed identity to structural proteins from picorna-like viruses. The amino acid sequence was most identical to SINV-1 (97%), followed by the Kashmir bee virus (KBV, 30%), and acute bee paralysis virus (ABPV, 29%) (Table 5).

TABLE 4

Oligonucleotide primers and their annealing temperatures.

| Designation | Oligonucleotide 5' > 3' |
|---|---|
| p58 | GCGATAGGTTAGCTTTAAGTACAATTGGTG SEQ ID NO 22 |
| p59 | TCCCAATGTGCAATAAACACCTTCA SEQ ID NO 23 |
| p62 | GGAAGTCATTACGTGGTCGAAAACG SEQ ID NO 2 |
| p63 | CGTCCTGTATGAAAACCGGTCTTTACCACAGAAATCTTA SEQ ID NO 3 |
| p102 | CGCCTTAGGATTCGTTAGATACTCACCCG SEQ ID NO 24 |
| p114 | CTTGATCGGGCAGGACAAATTC SEQ ID NO 25 |
| p116 | GAACGCTGATAACCAATGAGCC SEQ ID NO 26 |
| p117 | CACTCCATACAACATTTGTAATAAAGATTTAATT SEQ ID NO 27 |
| p118 | CCAATACTGAAACAACTGAGACGT SEQ ID NO 28 |
| p137 | GTCACATCACGTCGGTGTCGT SEQ ID NO 8 |
| p161 | GCGCGTGAATAAGATGACATTGCTTCCGAATCTG SEQ ID NO 29 |
| p188 | CTTAATTGTAATTTACTTGAATATGCGTTTGC SEQ ID NO 30 |
| p189 | GTATCTAACGAATCCTAAGGCGGATTG SEQ ID NO 31 |
| p190 | CAATCCGCCTTAGGATTCGTTAGATAC SEQ ID NO 32 |
| p191 | CGGATCTTATGAGTGAAGACACACCAG SEQ ID NO 33 |
| p193 | CAACCTCTGCTTCCCACGCAC SEQ ID NO 34 |
| p221 | GATGGTCTCGACCAAATGATATGGAG SEQ ID NO 35 |
| p222 | ATGAAGATATGAAGGTGTTTATTGCACATTG SEQ ID NO 36 |
| p341 | CACATAAGGGATATTGTCCCCATG SEQ ID NO 37 |
| p343 | TGGACGAGACGGATCTTATGAGTG SEQ ID NO 38 |
| 3' Primer | GCTGTCAACGATACGCTACGTAACG SEQ ID NO 39 |

TABLE 5

Comparative identities of SINV-1A amino acid sequences with corresponding sequences form other positive strand RNA viruses.

| Virus | Identity (%) | Accession No. |
|---|---|---|
| Solenopsis invicta virus 1 | 97.4 | AY634314 |
| Kashmir bee virus | 30.0 | NC004807 |
| Acute bee paralysis virus | 28.5 | NC002548 |
| Drosophila C virus | 16.2 | NC001834 |
| Triatoma virus | 14.8 | NC003783 |
| Black queen cell virus | 14.5 | NC003784 |
| Sacbrood virus | 12.1 | NC002066 |
| Hepatitus A virus | 11.7 | NC001489 |
| Cow-pea mosaic virus | 10.3 | NC003550 |

EXAMPLE 5

A field survey was conducted to examine the extent of SINV-1 and SINV-1A infection and co-infection among *S. invicta* nests from four locations around Gainesville, Fla. Ten nests were sampled from 4 different areas in Gainesville (n=40, Table 2). One-step RT-PCR with species/genotype-specific oligonucleotide primers was used to identify virus-infected *S. invicta* nests. Samples of worker caste ants were collected as described above in Example 1. RNA was extracted from about 20-50 workers using Trizol reagent according to manufacturer's instructions (Invitrogen). cDNA was synthesized and subsequently amplified using the One-Step RT-PCR kit (Invitrogen) with oligonucleotide primers p117-SEQ ID NO 27 and p118-SEQ ID NO 28 (SINV-1A specific) and p114-SEQ ID NO 25 and p116-SEQ ID NO 26 (SINV-1 specific) (Table 4). Samples were considered positive for each virus when a visible amplicon of anticipated size (about 646 nt for SINV-1 and about 153 nt for SINV-1A) was present after separation on about a 1.2% agarose gel stained with ethidium bromide. RT-PCR was conducted in a PTC 100 thermal cycler (MJ Research, Waltham, Mass.) under the following optimized temperature regime:

1 cycle at about 45° C. for about 30 minutes
1 cycle at about 94° C. for about 2 minutes
35 cycles at about 94° C. for about 15 seconds
1 cycle at about 54° C. for about 15 seconds
1 cycle at about 68° C. for about 30 seconds
Elongation step at about 68° C. for about 5 minutes In an attempt to gain additional insight into whether SINV-1A was a genotype or distinct species, oligonucleotide primers were designed to conserved areas, i.e., in common) of the 3'-end of the SINV-1 and SINV-1A sequences (p341-SEQ ID NO 37 and p343-SEQ ID NO 38, Table 4). These common primers were used for RT-PCR with representative ant colonies infected exclusively with either SINV-1 or SINV-1A (n=3); the resulting amplicons were subjected to analysis. Amplicons generated with the common primers from SINV-1 and SINV-1A-infected ant colonies were digested separately with AvaI and BglII, separated on about a 1.2% agarose gel and visualized by ethidium bromide staining.

In addition, colonies identified as being negative, i.e., no amplification, for infection by either SINV-1 or SINV-1A, as determined previously by RT-PCR and virus-specific primers, were subjected to a second RT-PCR with the common primers p341-SEQ ID NO 37 and p343-SEQ ID NO 38 (Table 4) to possibly identify additional species or genotypes.

A separate survey of monogyne and polygyne ants was conducted to determine if there was a social form-specific virus/genotype. Ant samples were taken from suspected monogyne- and polygyne-predominant areas and evaluated for infection with SINV-1 and SINV-1A as described above in this example. These samples were concomitantly evaluated by PCR to determine the social form of the nest. Social form was determined with PCR by exploiting nucleotide differences between the 2 gp-9 alleles: Gp-9$^B$, Gp-9$^b$, found in North American *S. invicta* (Krieger and Ross, Science, Volume 295, 328-323, 2002) by the method described by Valles and Porter (Insect. Soc., Volume 50, 199-200, 2003; herein incorporated by reference).

An RT-PCR-based survey for SINV-1 and SINV-1A using RNA extracts of *S. invicta* collected around Gainesville, Fla., revealed a mean colony infestation rate of bout 25% by SINV-1 and about 55% by SINV-1A (Table 6). Among 40 nests surveyed, infection rates among the four different sites ranged from about 10-40% for SINV-1 and about 40-70% for SINV-1A (Table 6). Both SINV-1 and SINV-1A were found to co-infect about 17.5% of the nests surveyed. It was not determined if individual ants were infected with both SINV-1 and SINV-1A.

Figure 4A:
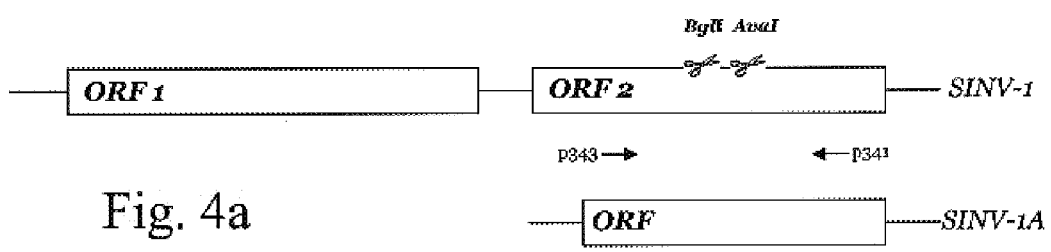
FIG. 4A is a schematic diagram of SINV-1 and SINV-1A genomes. ORFs are shown in open boxes. Conserved oligonucleotide primer positions are indicated by p341 and p343. Restriction positions unique to SINV-1 are approximated with scissor symbols.
Figure 4B:
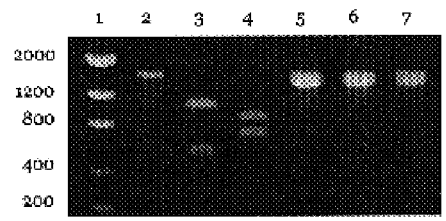
FIG. 4B is a photograph showing restriction fragment length polymorphism (RFLP) of a portion of the SINV-1 and SINV-1A genomes amplified with primers p341 and p343 and restriction digested with AvaI and BglII. Lane assignments are as follows: Lane 1: molecular weight markers; Lane 2: SINV-1 undigested; Lane 3: SINV-1 AvaI-digested; Lane 4: SINV-1 BglII-digested; Lane 5: SINV-1A undigested; Lane 6: SINV-1A AvaI-digested; and Lane 7: SINV-1A BglII-digested.

RFLP analysis of about a 1584 nucleotide amplicon at the 3'-end of the genomes produced with primers p341 (SEQ ID NO 37) and p343 (SEQ ID NO 38) form SINV-1 and SINV-1A-infected fire ants corroborated sequence data assembled for each species/genotype (FIG. 4). Digestion of this amplicon from SINV-1-infected fire ants with AvaI and BglII produced bands of approximately 550 and 1030, and 710 and 870 nucleotides in length, respectively. Conversely, the corresponding amplicon from SINV-1A-infected fire ants was not cut by either AvaI or BglII. All three replicates from different colonies of fire ants produced the same banding patterns and no amplicons were produced from uninfected ants.

RNA from colonies yielding no amplicon when utilizing SINV-1- and SINV-1A-specific primers, i.e., uninfected, was subsequently used with conserved primers (p341-SEQ ID NO 37 and p343-SEQ ID NO 38) in RT-PCR to possibly identify new viruses or genotypes related to SINV-1 and SINV-1A. In every instance (n=15), no amplification was observed with conserved primers.

SINV-1 and SINV-1A were found in monogyne and polygyne nests. Infection by either virus does not appear to be limited to a specific social form (Data not shown).

TABLE 6

Field Survey results of SINV-1 and SINV-1A infection of *S. invicta* from locations in Gainesville, Florida.

| Location (latitude/longitude) | SINV-1 infection (%) | SINV-1A infection (%) | Co-infection (%) |
|---|---|---|---|
| N29° 35.342', W082° 20.332' | 20 | 50 | 10 |
| N29° 45.824', W082° 24.352' | 30 | 40 | 20 |
| N29° 39.1', W082° 15.6' | 40 | 70 | 40 |
| N29° 40.128', W082° 31.395' | 10 | 60 | 0 |

EXAMPLE 7

To evaluate the efficacy of *Solenopsis invicta* virus complex (SINV-1 and genotypes), uninfected monogyne nests (n=6) initiated by newly mated queens were identified by RT-PCR with oligonucleotide primers designed to the 2 characterized genotypes:

p114 5'CTTGATCGGGCAGGACAAATTC SEQ ID NO 25 p116 5'GAACGCTGATAACCAATGAGCC SEQ ID NO 26 p117 5'CACTCCATACAACATTTGTAATAAA-GATTTAATT SEQ ID NO 27 p118 5'CCAATACTGAAACAACTGAGACACG SEQ ID NO 28

RT-PCR was conducted in a PTC 100 thermal cycler (MJ Research, Waltham, Mass.) under the following optimized temperature regime:

1 cycle at about 45° C. for about 30 minutes
1 cycle at about 94° C. for about 2 minutes
35 cycles at about 94° C. for about 15 seconds
1 cycle at about 54° C. for about 15 seconds
1 cycle at about 68° C. for about 35 seconds
Elongation step at about 68° C. for about 15 minutes.

The colonies were comprised of about 40-60 ml of brood, about 40,000-60,000 workers, and a single inseminated queen. Three colonies were used as control and 3 colonies were treated with virus-infected ants. Each colony was randomly assigned and paired. Colonies were infected as described above in Example 4. Approximately 300 workers from an SINV-infected colony were homogenized in an equal volume of water and immediately placed onto a mixture of approximately 3 grams of boiled chicken egg yolks and approximately 15 frozen crickets. The control colonies were treated similarly except uninfected ants were used. About 30 workers from treated and control colonies were removed periodically and tested for known SINV genotypes by RT-PCR. Concomitantly, the colonies were quantitatively assessed by determining the volume of brood and number of workers using a standard rating method described previously (Banks et al., J. Econ. Entomol., Volume 81, 83-87, 1988; herein incorporated by reference).

Figure 5:
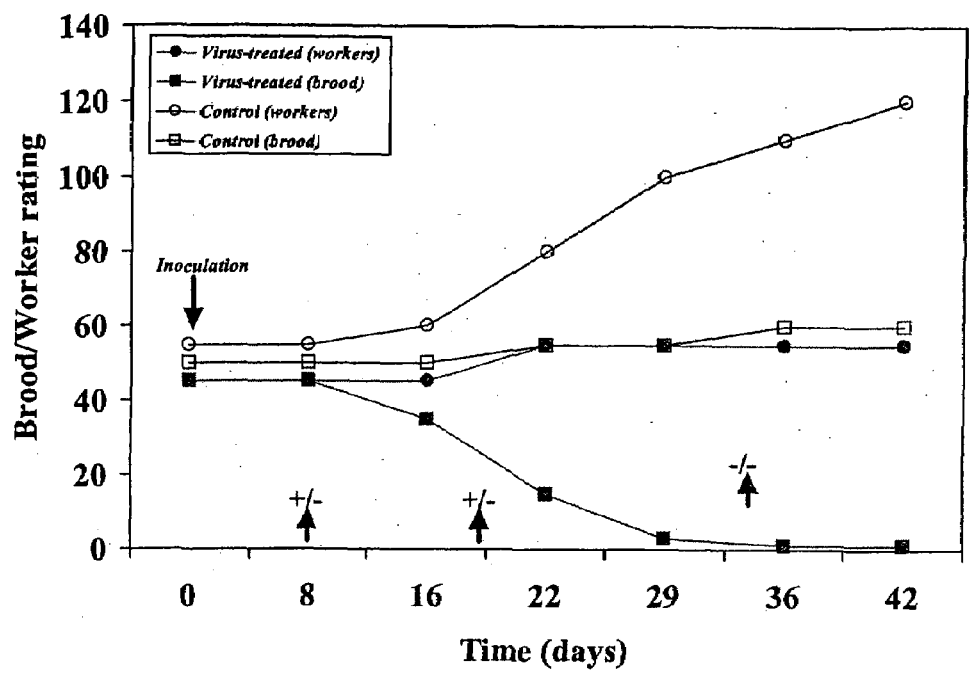
FIG. 5 is a graph showing the brood rating (ml) and worker rating (X $10^3$) of *Solenopsis invicta* fire ant colonies 10 and 14 over about a 42 day period. Colony 10 (red lines) was inoculated with *Solenopsis invicta* virus on day 0. Up-arrows indicate time points at which viral detection was assessed in each colony (treated and control) and the corresponding +/− symbols indicate positive and negative viral detection, respectively.
Figure 6:
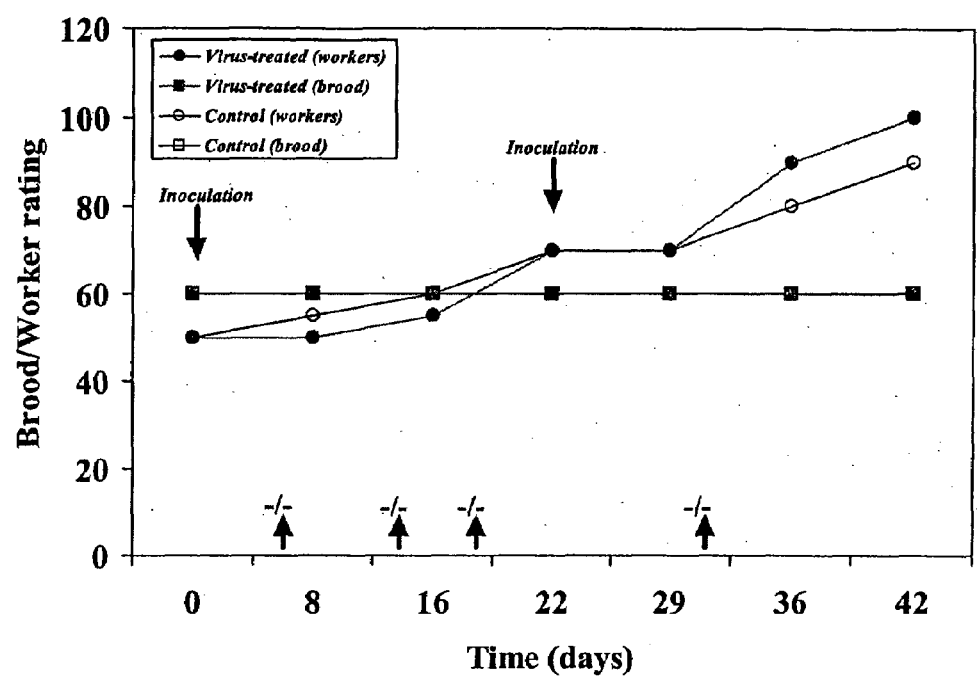
FIG. 6 is a graph showing the brood rating (ml) and worker rating (X $10^3$) of *Solenopsis invicta* fire ant colonies 12 and 13 over a 42-day period. Colony 12 was inoculated with *Solenopsis invicta* virus on day 0. Up arrows indicate time points at which viral detection was assessed in each colony (treated and control) and the corresponding +/− symbols indicate positive and negative viral detection, respectively.
Figure 7:
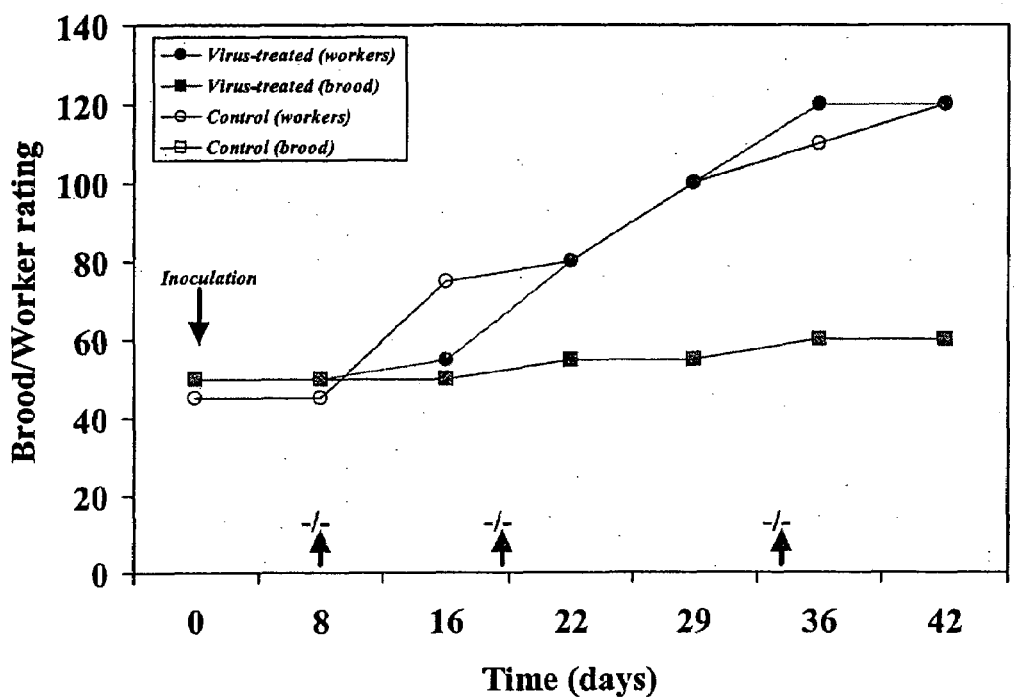
FIG. 7 is a graph showing the brood rating (ml) and worker rating (X $10^3$) of *Solenopsis invicta* fire ant colonies 3 and 6 over a 42-day period. Up arrows indicate time points at which viral detection was assessed in each colony (treated and control) and the corresponding +/− symbols indicate positive and negative viral detection, respectively.

FIGS. 5-7 illustrate the transmission and efficacy results. Three of the six colonies were inoculated with the virus at day 0 of the experiment as indicated. Viral transmission was successful in about 67% of the treatments (Colonies 10 and 12, FIGS. 5 and 6, respectively). The infection sustained itself in colony 10 for at least about 2 weeks (FIG. 5) and was associated with a precipitous and significant decline in brood. The brood rating in colony 10 declined from about 45 ml to less than 3 ml in about 28 days. Colony 10 never recovered and lingered with only adult ants over subsequent months. Fire ant colonies cannot survive without brood because all digestion of solid food is done by the fourth instars. Therefore, once the brood was killed off, the colony could never recover. The brood rating for the corresponding control colony 14 increased slightly over the same period as is observed in normal, healthy laboratory colonies.

Colony 12 (FIG. 6) appeared to be infected for about 2 consecutive weeks. However, the infection did not sustain itself in the population and possibly never achieved replication. The results from Colony 12 corroborate the conclusion that sustained viral infection and most likely replication was responsible for the decline and ultimate death of Colony 10 (FIG. 5). A second inoculation attempt was made against Colony 12 on day 22 but viral transmission did not occur (FIG. 7). Colony 3 remained as healthy as the control Colony 6.

Immune response of the ants must be considered when interpreting these results. Some ants, as any organism, are going to be more susceptible to infection and detrimental effects of a pathogen such as SINV than others. A range of susceptibility would be anticipated. Therefore, not all colonies would be expected to become infected when challenged. Moreover, previous exposure to similar pathogens, such as Cripaviruses, can provide protection to an insect challenged by a similar pathogen later.

EXAMPLE 8

External stressors may be required to initiate replication of virus and result in brood death. To test this, 2 newly-mated queen colonies with brood ratings of about 50-60 ml, were infected with SINV-1 or SINV-1A. The virus-infected colonies and one control colony were treated with approximately 15 grams of Extinguish commercial formulation of methoprene (Wellmark, Schaumburg, Ill.) provided in a plastic weigh boat and monitored for about 35 days. Brood and worker ratings were assessed every 7 days after treatment by the method of Banks et al (1988, supra).

Figure 8:
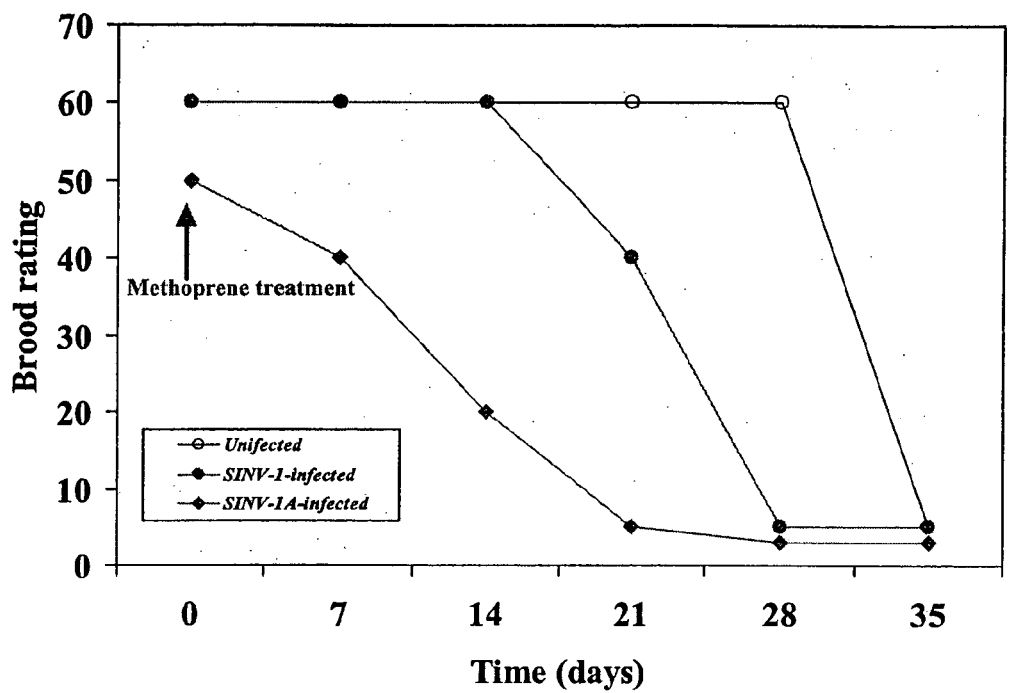
FIG. 8 is a graph showing the brood rating (ml) of *Solenopsis invicta* fire ant colonies 8, 9, and 17 over a 35-day period. Colonies 17 (♦) and 8 (●) exhibited sustained infections with SINV-1A and SINV-1 at the beginning of the experiment. Colony 9 (○) served as the control group. The up-arrow indicated the time at which each colony was treated with the insecticide, methoprene.

Brood were killed 1-3 weeks faster in two SINV-infected colonies treated with Methoprene than in an uninfected colony (FIG. 8). Note that among two SINV-infected colonies treated with methoprene, brood began dying in as little as about one week after treatment while no effects were detected in the uninfected colony for about four weeks.

EXAMPLE 9

In order to understand effects of SINV against *Solenopsis invicta* in the field, two sites in Gainesville, Fla., were monitored for 7 months for SINV prevalence. One site was located on US441 on the north side of Paines Prairie State Preserve. The other site was located at the East University Avenue/SR26 junction. Ten fire ant nests from each site per month were sampled as described in Example 1 and used in subsequent RT-PCR analyses as described above in Example 7. Simple observation was used to characterize the mound density each month.

Figure 9:
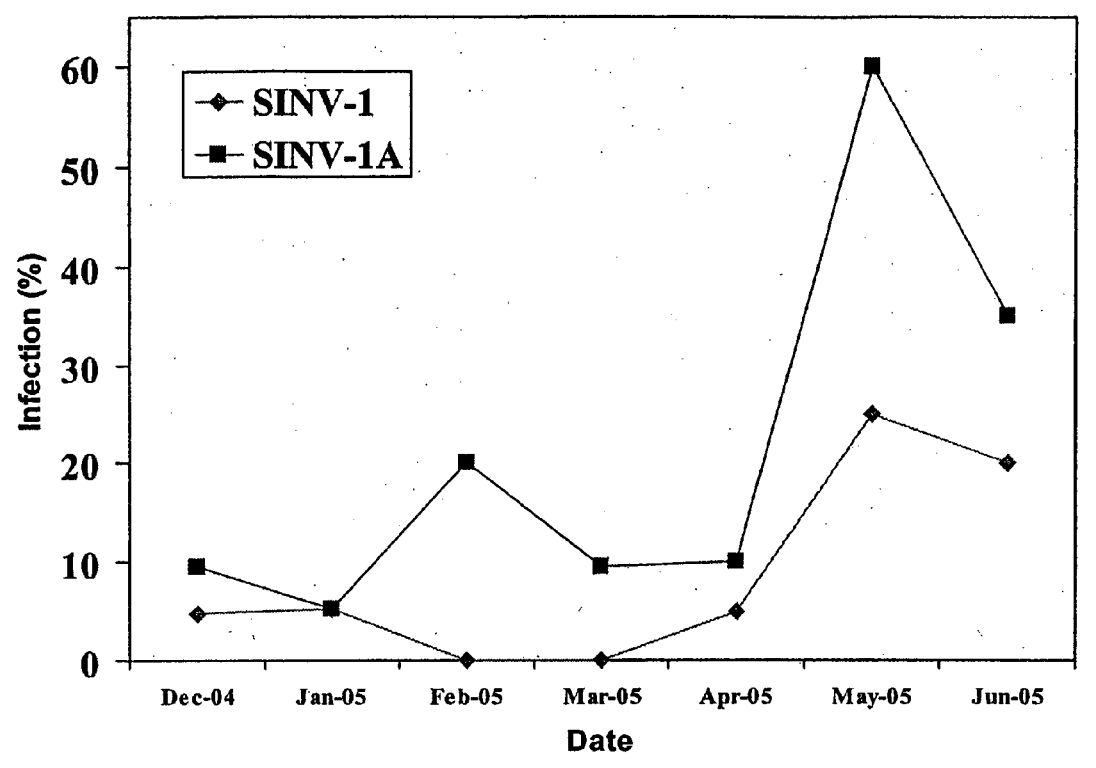

FIG. 9 illustrates the seasonal prevalence or phenology of the characterized genotypes, SINV-1 and SINV-1A. The prevalence of the virus remained fairly constant, averaging between 0% and about 60% during the winter and early spring months (December to April). However, a sharp increase in viral prevalence to about 60% for SINV-1A and about 28% for SINV-1 was observed in May. The fire ant nest density was reduced by approximately 50% in June as compared to May immediately following the spike in viral prevalence that occurred in May.

The foregoing detailed description is for the purpose of illustration. Such detail is solely for that purpose and those skilled in the art can make variations without departing from the spirit and scope of the invention.

We claim:

1. A *Solenopsis invicta* virus having the nucleic acid sequence as set forth in SEQ ID NO 1.

2. An isolated nucleic acid sequence encoding open reading frame 2 of *Solenopsis invicta* virus having the sequence as set forth in SEQ ID NO 21.

3. A biocontrol composition comprising:

(a) an effective amount of a *Solenopsis invicta* virus preparation to at least reduce the number of fire ants in a colony, and (b) a carrier wherein said virus has the nucleic acid sequence as set forth in SEQ ID NO 1.

4. The composition of claim 3 wherein said carrier is a food source for said ants.

5. The composition of claim 4 wherein said food source is selected from the group consisting of insects, cooked egg yolk, corn cob grits, soybean oil, extruded corn pellets, and mixtures thereof.

6. A biocontrol composition comprising:

(c) an effective amount of a *Solenopsis invicta* virus preparation to at least reduce the number of fire ants in a colony, and (d) a carrier wherein said virus has an open reading frame having the sequence as set forth in SEQ ID NO 21.

* * * * *